US010406374B2

(12) United States Patent
Liu et al.

(10) Patent No.: US 10,406,374 B2
(45) Date of Patent: Sep. 10, 2019

(54) CONFIDENCE ANALYZER FOR AN AUTOMATED EXTERNAL DEFIBRILLATOR (AED) WITH DUAL ECG ANALYSIS ALGORITHMS

(71) Applicant: KONINKLIJKE PHILIPS N.V., Eindhoven (NL)

(72) Inventors: Chenguang Liu, Bothell, WA (US); Stacy Earl Gehman, Seattle, WA (US); Dawn Blilie Jorgenson, Mercer Island, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/529,723

(22) PCT Filed: Dec. 9, 2015

(86) PCT No.: PCT/IB2015/059460
§ 371 (c)(1),
(2) Date: May 25, 2017

(87) PCT Pub. No.: WO2016/092480
PCT Pub. Date: Jun. 16, 2016

(65) Prior Publication Data
US 2017/0361120 A1 Dec. 21, 2017

Related U.S. Application Data

(60) Provisional application No. 62/090,950, filed on Dec. 12, 2014.

(51) Int. Cl.
A61N 1/00 (2006.01)
A61N 1/39 (2006.01)
(Continued)

(52) U.S. Cl.
CPC ............ *A61N 1/3987* (2013.01); *A61B 5/046* (2013.01); *A61B 5/04012* (2013.01);
(Continued)

(58) Field of Classification Search
USPC ............................................................ 607/5
See application file for complete search history.

(56) References Cited

U.S. PATENT DOCUMENTS 5,957,856 A 9/1999 Weil et al.
6,356,785 B1 3/2002 Snyder et al.
(Continued)

FOREIGN PATENT DOCUMENTS

EP 2172245 A1 4/2010
EP 2319409 A1 5/2011
(Continued)

*Primary Examiner* — Nicole F Lavert

(57) ABSTRACT

A defibrillator and method for using a defibrillator which adopts an ECG analysis algorithm that can detect a cardiac arrhythmia in the presence of noise artifact induced by cardio pulmonary resuscitation (CPR) compressions. The apparatus and method includes a confidence analyzer circuit which determines the confidence level of an electrotherapy shock decision based on the detection. If the confidence level is low, the apparatus adjusts its shock decision criteria.

14 Claims, 20 Drawing Sheets

(51) Int. Cl.
*A61B 5/00* (2006.01)
*A61B 5/046* (2006.01)
*A61B 5/04* (2006.01)
*A61B 5/0464* (2006.01)

(52) U.S. Cl.
CPC .............. *A61B 5/4836* (2013.01); *A61B 5/72* (2013.01); *A61B 5/7217* (2013.01); *A61N 1/3904* (2017.08); *A61N 1/3925* (2013.01); *A61N 1/3993* (2013.01); *A61B 5/0464* (2013.01)

(56) References Cited

U.S. PATENT DOCUMENTS

| | | | |
|---|---|---|---|
| 6,553,257 | B2 | 4/2003 | Snyder et al. |
| 6,671,547 | B2 | 12/2003 | Lyster et al. |
| 6,754,528 | B2 | 6/2004 | Bardy et al. |
| 7,171,269 | B1 | 1/2007 | Addison et al. |
| 7,463,922 | B1 | 12/2008 | Snyder et al. |
| 8,335,559 | B2 | 12/2012 | Tan et al. |
| 8,626,286 | B2 | 1/2014 | Yamaguchi et al. |
| 8,825,154 | B2 | 9/2014 | Jorgenson et al. |
| 2002/0133197 | A1 | 9/2002 | Snyder et al. |
| 2003/0212437 | A1 | 11/2003 | Rock et al. |
| 2004/0162585 | A1 | 8/2004 | Elghazzawi et al. |
| 2005/0131465 | A1* | 6/2005 | Freeman ............... A61H 31/005 607/5 |
| 2006/0058848 | A1 | 3/2006 | Piraino et al. |
| 2006/0229679 | A1 | 10/2006 | Joo |
| 2008/0208070 | A1 | 8/2008 | Snyder et al. |
| 2008/0215103 | A1 | 9/2008 | Powers |
| 2011/0202100 | A1* | 8/2011 | Tan ....................... A61H 31/005 607/6 |
| 2011/0224746 | A1 | 9/2011 | Didon |
| 2012/0226178 | A1 | 9/2012 | Freeeman et al. |
| 2013/0053649 | A1 | 2/2013 | Elghazzawi et al. |
| 2013/0218057 | A1 | 8/2013 | Jorgenson et al. |
| 2013/0282068 | A1 | 10/2013 | Sagiroglu et al. |
| 2013/0282072 | A1 | 10/2013 | Abdeen et al. |
| 2014/0066799 | A1 | 3/2014 | Sherman et al. |
| 2014/0088374 | A1 | 3/2014 | Sullivan et al. |
| 2014/0100497 | A1 | 4/2014 | Hayashi et al. |
| 2014/0107541 | A1 | 4/2014 | Sullivan et al. |
| 2014/0277225 | A1 | 9/2014 | Quan et al. |
| 2014/0277228 | A1 | 9/2014 | Quan et al. |
| 2017/0361120 | A1 | 12/2017 | Liu et al. |

FOREIGN PATENT DOCUMENTS

| | | |
|---|---|---|
| EP | 2653189 A1 | 10/2013 |
| EP | 2716325 A1 | 4/2014 |
| JP | 2007502674 A | 2/2007 |
| JP | 2015205055 A | 11/2015 |
| WO | 2005018738 A1 | 3/2005 |
| WO | 2007069162 A1 | 6/2007 |
| WO | 2007089225 A1 | 8/2007 |
| WO | 2008086496 A2 | 7/2008 |
| WO | 2011100507 A1 | 8/2011 |
| WO | 2012059846 A1 | 5/2012 |
| WO | 2012127380 A1 | 9/2012 |
| WO | 2013003852 A1 | 1/2013 |
| WO | 2013003852 A2 | 1/2013 |
| WO | 2013179234 A1 | 12/2013 |
| WO | 2014141056 A2 | 9/2014 |
| WO | 2014141080 A1 | 9/2014 |
| WO | 2015101911 A1 | 7/2015 |
| WO | 2016091948 A1 | 6/2016 |
| WO | 2016092477 A1 | 6/2016 |
| WO | 2016097934 A1 | 6/2016 |
| WO | 2016097938 A1 | 6/2016 |

* cited by examiner

1600

CONFIDENCE ANALYZER FOR AN AUTOMATED EXTERNAL DEFIBRILLATOR (AED) WITH DUAL ECG ANALYSIS ALGORITHMS

CROSS-REFERENCE TO PRIOR APPLICATIONS

This application is the U.S. National Phase application under 35 U.S.C. § 371 of International Application No. PCT/IB2015/059460, filed on Dec. 9, 2015, which claims the benefit of U.S. Provisional Patent Application No. 62/090,950, filed on Dec. 12, 2014. These applications are hereby incorporated by reference herein.

BACKGROUND

This invention relates to an improved apparatus and method for treating victims of cardiac arrest, and in particular for those patients who require a treatment regime consisting of cardiopulmonary resuscitation (CPR) and defibrillation electrotherapy.

A defibrillator delivers a high-voltage impulse to the heart in order to restore normal rhythm and contractile function in patients who are experiencing arrhythmia, such as ventricular fibrillation ("VF") or ventricular tachycardia ("VT") that is not accompanied by spontaneous circulation. There are several classes of defibrillators, including manual defibrillators and automated external defibrillators ("AEDs"). AEDs differ from manual defibrillators in that AEDs can automatically analyze the electrocardiogram ("ECG") rhythm to decide if defibrillation is necessary. After deciding that a shock is needed, the AED arms itself for delivering an electrotherapeutic shock, and then the AED advises the user to press a shock button to deliver the defibrillation shock. An AED that operates in this manner is called semi-automatic. Fully automatic AEDs deliver the defibrillation shock without any user input. Fully automatic AEDs are generally called fully automatic defibrillators in order to reduce confusion in terminology.

FIG. 1 is an illustration of a defibrillator 1 being applied by a user 2 to resuscitate a patient 4 suffering from cardiac arrest. The defibrillator 1 may be in the form of an AED or a fully automatic defibrillator capable of being used by a first responder. The defibrillator 1 may also be in the form of a manual defibrillator for use by paramedics or other highly trained medical personnel. Two or more electrodes 6 are applied across the chest of the patient 4 by the user 2 in order to acquire an ECG signal from the patient's heart. The defibrillator 1 then analyzes the ECG signal for signs of arrhythmia with a shock analysis algorithm. Only if a shockable rhythm, such as VF or a non-perfusing ventricular tachycardia (VT), is detected does the defibrillator 1 arm itself to deliver a high voltage shock. The defibrillator 1 signals the user 2 via aural or visual prompts that a shock is advised. The user 2 then presses a shock button on the defibrillator 1 to deliver a defibrillation shock.

It is well established that the quicker that circulation can be restored (via CPR and defibrillation) after the onset of VF, the better the chances that the patient will survive the event. For this reason, many AEDs such as the one shown in FIG. 1 also incorporate a user interface including audible, aural, and visual prompting for guiding a user through a programmed sequence of CPR and defibrillation shocks. The user interface may include detailed aural prompting for properly applying CPR compressions, an audible metronome for guiding the user to the proper rate of compressions, a visual display to show the state and progress of the event, annunciators, flashing lights, and the like. The sequence is pre-programmed into the device in accordance with a protocol established by the local medical authority.

There are several ECG analysis algorithms which automatically analyze a patient's ECG to decide if a defibrillating shock is appropriate to treat the underlying cardiac rhythm. One such algorithm is generally described by Lyster et al. in the co-assigned U.S. Pat. No. 6,671,547 entitled "Adaptive analysis method for an electrotherapy device and apparatus" and herein incorporated by reference. The described algorithm relates to the Patient Analysis System (PAS) algorithm that is currently employed in AEDs, such as the Heartstart™ FR3 AED manufactured by Koninklijke Philips, N.V. of Andover, Mass.

But PAS and other existing ECG algorithms for determining a shockable condition require relatively noise-free ECG signals. All existing protocol sequences require the cessation of CPR during analysis because CPR causes artifact in the ECG which can mask VF when it is occurring, or can appear as VF when VF is not occurring. The former condition causes an undesirable reduction in sensitivity of the analysis, while the latter condition causes an undesirable reduction in specificity of the analysis. Consequently, all existing protocols of CPR and defibrillation require periodic "hands-off" periods of at least several seconds to allow the defibrillator to analyze the ECG with sufficient accuracy to be safe, useful, and effective to the patient.

Several problems arise from the need to interrupt CPR for ECG analysis. It has been shown that interruptions in CPR compressions, even for just a few seconds, may reduce the likelihood of a successful resuscitation. Thus, the required cessation of CPR for ECG analysis prior to delivering a defibrillating shock may reduce the chances of a successful patient outcome. And the delay in resuming CPR after defibrillation in order to assess the success of the shock may also impact the patient outcome.

Several prior art solutions to this problem have been developed, all directed toward reducing the amount of delay. One solution, for example, is to remove CPR noise artifact from the ECG signal by the use of adaptive filtering. Co-assigned U.S. Pat. No. 6,553,257 by Snyder et al. entitled "Interactive Method of Performing Cardiopulmonary Resuscitation with Minimal Delay to Defibrillation Shocks", and herein incorporated by reference, describes such an adaptive filtering method.

Another alternative approach for analyzing ECG in the presence of CPR noise artifact involves wavelet transform analysis of ECG data streams. One example of this approach is described by Addison in U.S. Pat. No. 7,171,269 entitled "Method of Analysis of Medical Signals" and incorporated herein by reference. The '269 patent describes the use of wavelet transform analysis to decompose signals into heart and CPR-related signals. Another example of this approach is adopted by Coult et al. in International Patent Application No. PCT/US2012/045292 entitled "Systems and Methods for Analyzing Electrocardiograms to Detect Ventricular Fibrillation." There, an electrocardiogram signal is interrogated by a wavelet, such as a Morlet, Myers, or Mexican Hat wavelet, prior to being analyzed and stratified into a shockable or non-shockable ECG.

Unfortunately, many of the ECG analyzing techniques lack the accuracy necessary to reliably determine a shockable rhythm in the presence of CPR noise artifact while avoiding "false positive" shock decisions. These techniques are also susceptible to external electrical noise, such as line noise, and have not been adopted.

For these reasons, other solutions have been developed to shorten the amount of "hands-off" ECG time needed to accurately determine a shockable rhythm. Co-assigned U.S. Pat. No. 7,463,922 by Snyder et al. entitled "Circuit and method for analyzing a patient's heart function using overlapping analysis windows", also herein incorporated by reference, describes one such technique of using time-overlapped ECG data buffers to arrive at a quicker shock decision. Unfortunately, these prior art solutions serve only to reduce the delay time, but do not eliminate them entirely.

Another problem that arises from the existing inability to analyze ECG in the presence of artifact noise from CPR is that of refibrillation. A portion of patients that are successfully defibrillated, i.e. revert to an organized cardiac rhythm or asystole, subsequently re-enter VF several seconds to several minutes later. Some of these patients refibrillate during the fixed duration CPR period in which no ECG analysis is currently possible. Consequently, there is presently no treatment for addressing refibrillation except to wait for the protocol hands-off analysis period at the end of the CPR period. This delay in treating refibrillation is likely to be suboptimal for patient outcomes.

One-solution to the problem of refibrillation during CPR has been proposed, involving a measure of cardiac "vitality" during CPR. One such measure is the so-called "probability of Return of Spontaneous Circulation" (pROSC) score determined during CPR and described by Jorgenson et al. in U.S. patent application Ser. No. 13/881,380 entitled "Defibrillator with Dynamic Ongoing CPR Protocol", incorporated herein by reference.

Another measure for predicting VF is the so-called Amplitude Spectrum Area (AMSA) Score described by Quan et al. in U.S. patent application Ser. No. 14/211,681 entitled "Treatment Guidance Based on Victim Circulatory Status and Prior Shock Outcome". These approaches, however, only offer an indication of whether CPR should be discontinued to perform an ECG analysis for defibrillation purposes. Thus, additional delays can be induced by these solutions.

SUMMARY

The inventors have recognized the limitations afforded by the prior art, and have determined that what is needed is a technique for analyzing ECG in the presence of CPR noise artifact which provides a robust and reliable indication of a shockable rhythm. The needed technique must have sufficient sensitivity and specificity to eliminate delays between CPR and defibrillation, and to treat refibrillation quickly after it occurs. The technique must be computationally efficient such that it can be incorporated into a portable medical device which is used real-time during cardiac emergencies. The present inventors have developed such a technique.

In accordance with the principles of the present invention, a medical apparatus and method are described which improves the treatment for cardiac arrest. In particular, the apparatus is a monitor or defibrillator which incorporates an ECG analysis algorithm that can accurately identify a cardiac arrhythmia that is treatable by electrotherapy, even in the presence of noise artifact typically experienced during CPR. Such an algorithm permits a more efficient and effective delivery of electrotherapy while simultaneously increasing the effectiveness of CPR by reducing interruptions. The apparatus also includes a confidence analyzer circuit which determines a confidence level in a determined cardiac rhythm, and adjusts shock decision criteria if the confidence is low.

An improved method which also includes a confidence level calculating step during the ECG analyzing, and which adjusts shock decision criteria if the confidence level is low.

The apparatus and method thus provides for treatment using a combination of CPR and defibrillation shocks that provides a more accurate shock decision, especially for an ECG analysis that occurs in the presence of CPR-related signal noise artifact.

In accordance with the principles of the present invention, an AED for use during CPR is described comprising an input of an ECG signal, a user interface having at least one of an aural instruction output and a visual display, an ECG analyzer in communication with the input and operable to determine a shockable cardiac rhythm in the presence of CPR-related signal noise artifact from the input, and a confidence analyzer operable to determine a confidence level in the determined shockable cardiac rhythm. A processor is in communication with the user interface, the ECG analyzer and the confidence analyzer. The processor is operable to execute software instructions to adjust a shock decision criteria if the confidence level is less than a predetermined confidence threshold, decide that a shock is to be delivered by an electrotherapy delivery circuit based on the adjusted shock decision criteria, and arm an electrotherapy delivery circuit responsive to a shock delivery decision. The AED may adjust the shock decision criteria by, for example, increasing a minimum number of a shockable cardiac rhythm determinations from three to four required by the ECG analyzer prior to finalizing a shock delivery decision. Alternatively, the AED may adjust the shock decision criteria by first prompting a user to stop CPR via the AED user interface and then to confirm that a shock is to be delivered based on a second (PAS) ECG analyzer. The prompting may occur either during the ongoing CPR period or immediately at its conclusion. Indications of the confidence level may be provided by the user interface during these periods.

Also in accordance with the principles of the present invention, a method for controlling an electrotherapy output from a defibrillator during the application of CPR is described, comprising the steps of receiving an ECG signal data stream from two or more external electrodes in electrical contact with a patient, the ECG signal data comprising a cardiac signal characterized by corruption from a CPR compressions noise artifact, and obtaining an ECG signal data stream buffer, the buffer corresponding to a predetermined time segment. The method continues by analyzing the ECG signal data stream buffer to determine a shockable cardiac rhythm with a first ECG analysis algorithm, and calculating a confidence level of the determined shockable cardiac rhythm. The method then adjusts a shock decision criterion if the confidence level is less than a predetermined confidence threshold. Finally, the method decides that a shock is to be delivered by an electrotherapy delivery circuit based on the analyzing step and the adjusting step, and arms an electrotherapy delivery circuit responsive to the deciding step.

Alternative adjusting steps in the inventive method include increasing a minimum number of analyzing steps from three to four, or of switching to a different ECG analysis algorithm to provide a confirming shock decision. A user prompting step to stop CPR may be needed for optimal performance of the different ECG analysis algorithm.

IN THE DRAWINGS

FIGS. 17a, 17b, 17c, and 17d illustrate exemplary embodiments of a user input button and a visual display that displays information regarding the underlying state of the AED operation and contextual labels disposed adjacent the buttons.

Figure 18:
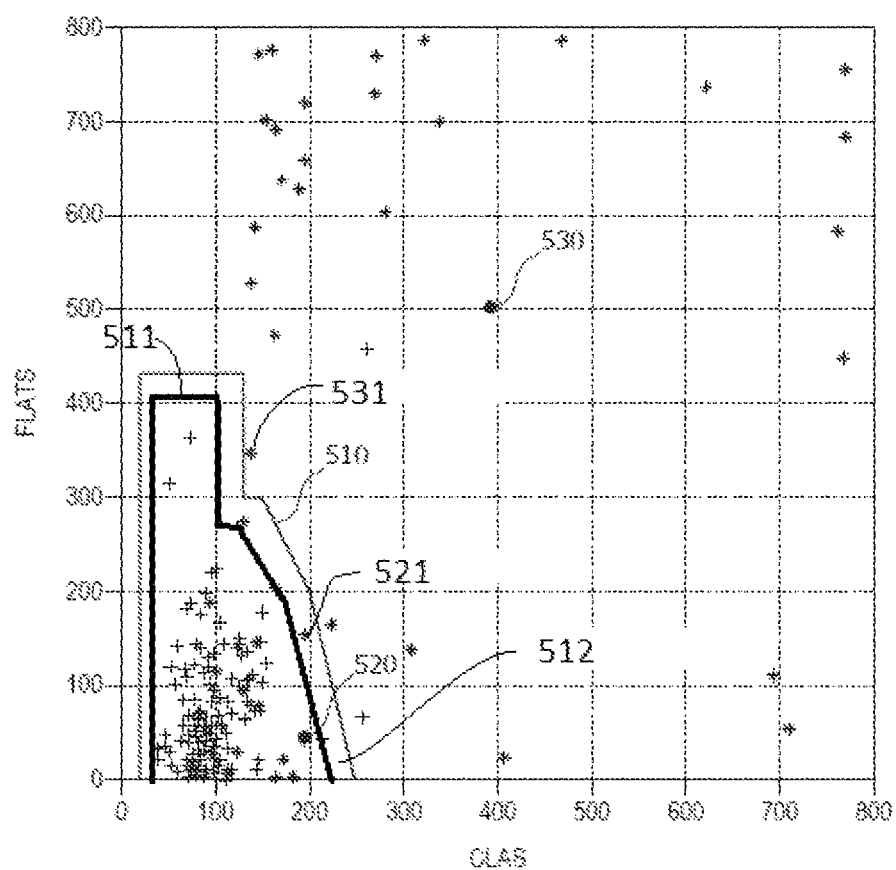

FIG. 18 illustrates another exemplary embodiment of a two-dimensional decision surface for classifying a corrupted ECG signal as VF or undecided, where the VF, i.e. shockable region is distinguished by low and high confidence regions.

Figure 19:
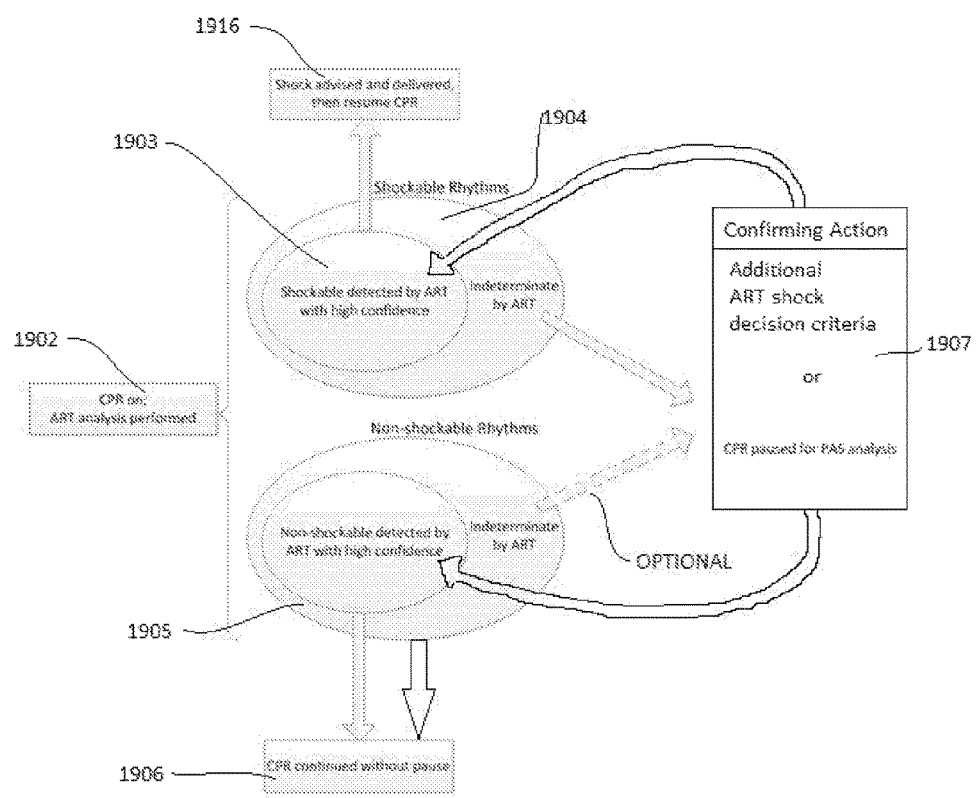

FIG. 19 illustrates a shock determination method flow process which incorporates a confidence analysis step prior to finalizing a shock determination.

DETAILED DESCRIPTION OF THE INVENTION

The inventive shock advisory algorithm, called the Optimized Arrhythmia Recognition Technology (ART), generally applies the principles of the afore-described wavelet transform analysis to a stream of ECG signals, but instead replaces the wavelet transform with a series of fixed-frequency band pass filters. The set of band pass filters is preferably constructed to have frequency windows shaped like the Gaussian windows that are used to produce traditional Morlet wavelets.

The ART algorithm suppresses CPR artifact related noise by selectively passing relatively high frequency components of a potentially corrupted ECG signal. ART is based on the inventors' realization that, while CPR and an organized cardiac rhythm can occur at similar repetition rates of about 1 to 2 Hz, typical CPR noise has relatively few high frequency components in its signal, i.e. the signal tends to be a rounded waveform. Cardiac activity tends to have relatively numerous high frequency components due to the rapid polarization and depolarization of the heart over a single cycle. It is these high frequency components that are to be captured and analyzed by ART.

Figure 1:
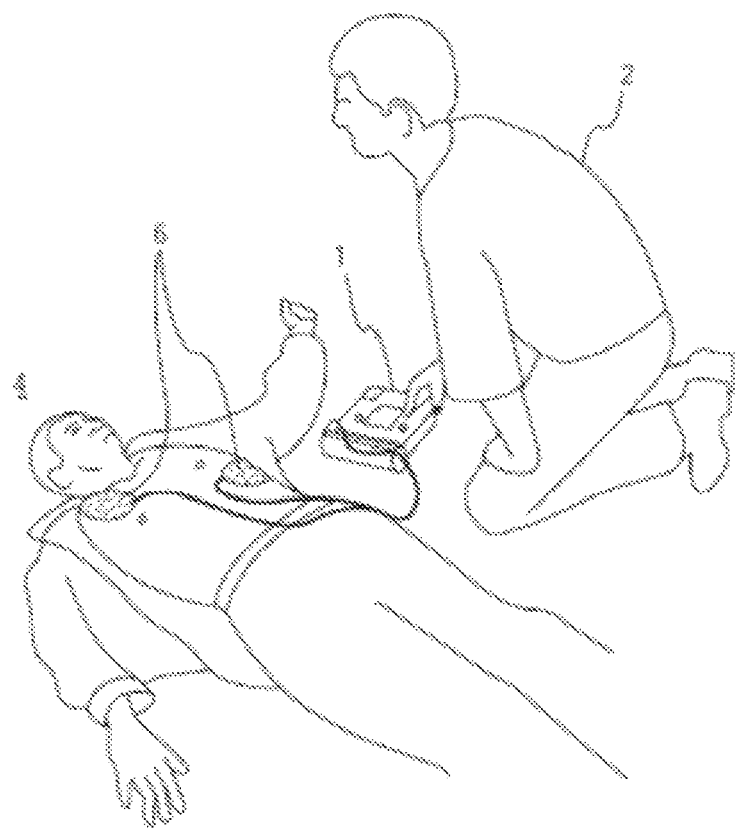
FIG. 1 illustrates a defibrillator and its use during a cardiac rescue, according to the prior art.
Figure 2A:
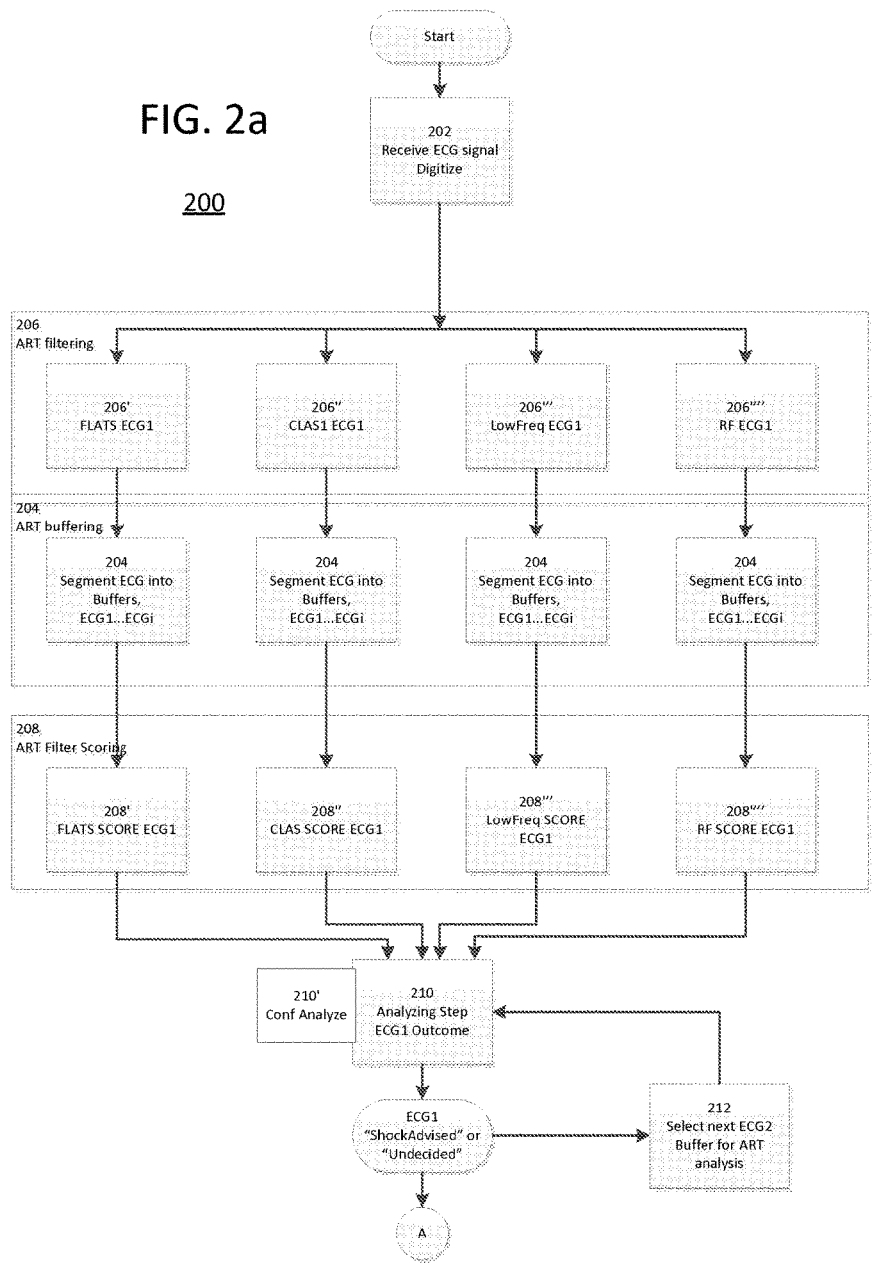
FIG. 2a illustrates one process flow embodiment of the inventive algorithm for analyzing ECG in the presence of noise artifact from CPR compressions.

Now turning to the illustrations, FIG. 2a illustrates a process flow embodiment of the inventive ART algorithm 200 for analyzing ECG in the presence of noise artifact from CPR compressions. At step 202, the method first receives an ECG signal, preferably from two or more electrodes which are arranged in electrical contact with a patient's skin. The ECG signal is a time-varying voltage whose source is the patient's heart as well as possibly voltages induced by CPR compressions being applied to the patient. The signal may also include other artifact signals that are external to the patient, such as patient jostling and motion, external electrical noise, etc. The ECG signal is preferably digitized into a stream of signal data.

At filtering step 206, the digitized ECG signal stream is processed through the ART filtering algorithm. Here, each data point in the signal stream is filtered through a set of first through fourth parallel filters at first through fourth parallel filtering steps 206' 206" 206'" and 206"", each having a different band-pass characteristic. Each filter is preferably a Finite Impulse Response filter. The number of filters and the band-pass characteristics of each filter may differ somewhat within the scope of the invention.

Figure 3:
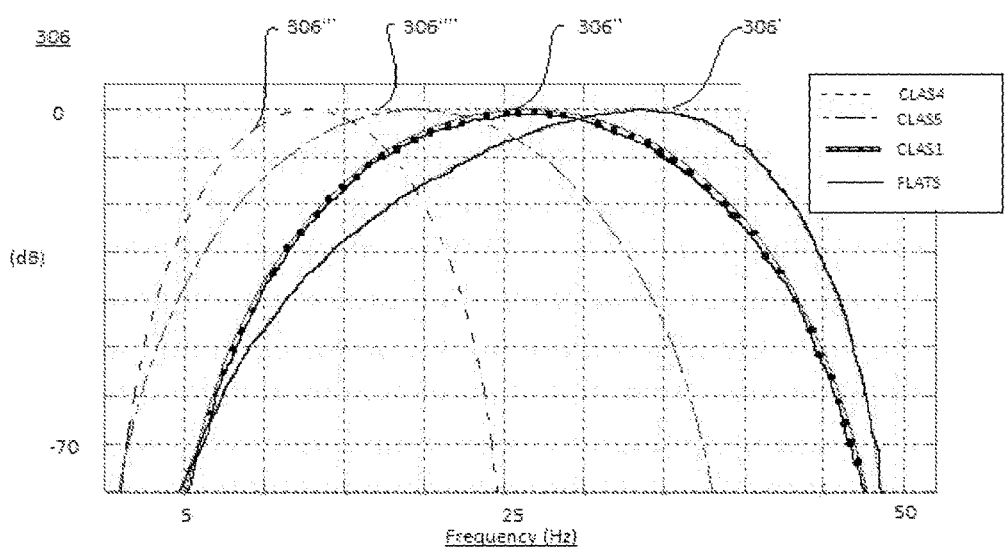
FIG. 3 illustrates the frequency characteristics of a set of filters for removing CPR artifact and other signal noise from an ECG signal, according to the present invention.

A preferred arrangement of ART filters 306 is as follows and is shown in FIG. 3. Four basic filters may be adopted, which generally apply to the corresponding filter steps 206 in FIG. 2a. One, called FLATS 306', and another one, called CLAS1 306", tend to pass higher frequency components of the ECG signal, and may present features to 1) distinguish ventricular fibrillation from asystolic rhythms; 2) distinguish ventricular fibrillation from organized cardiac activities; 3) distinguish ventricular fibrillation from asystolic rhythms and organized cardiac activities. Both FLATS 306' and CLAS1 306" tend to attenuate data at frequencies associated with CPR artifact such that their outputs are of cardiac information that is separated from the CPR compression noise signal. As can be seen in the illustrative and exemplary embodiment of FIG. 3, FLATS 306' has a center frequency of about 35 Hz, and CLAS1 306" has a center frequency of about 25 Hz. CLAS5 306'" is arranged to reject radio frequency (RF) noise. And CLAS4 306'" may be arranged to pass lower frequency components that are useful for rejecting false positive indications of VF caused by certain artifacts, for instance, due to transportation, muscle contraction, radio frequency interference, etc.

In the preferred arrangement, the digitized ECG signal input results in four filtered ECG signal stream outputs.

Figure 4:
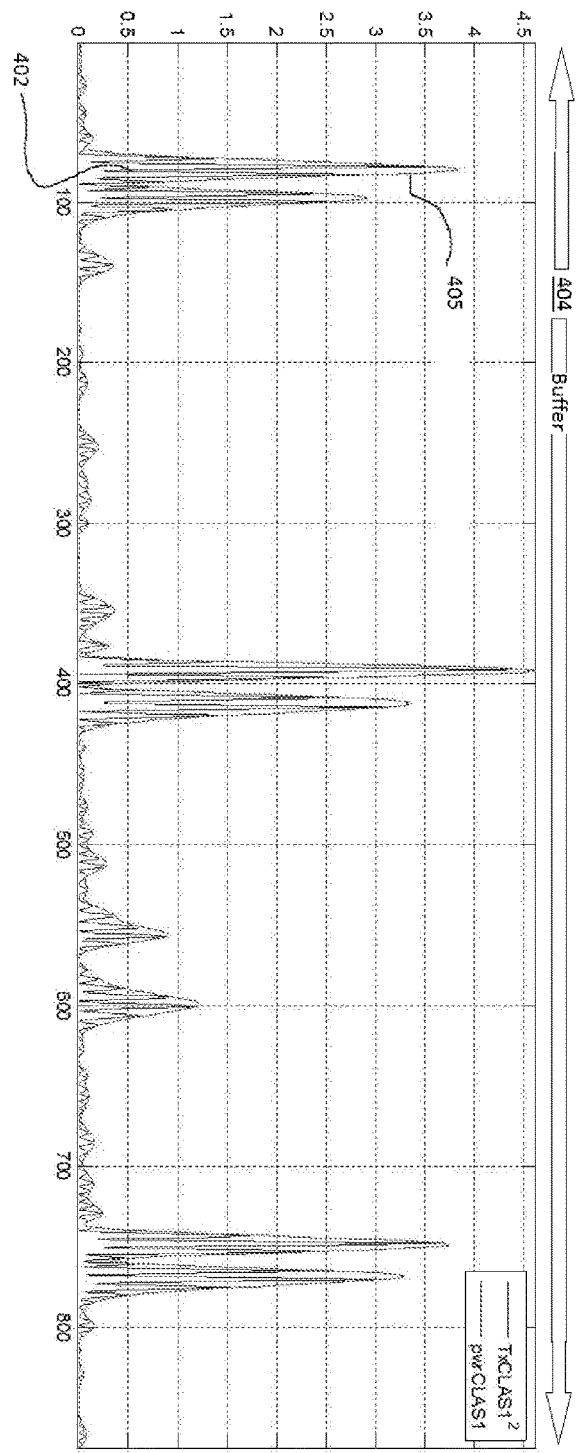
FIG. 4 illustrates an example ECG output buffer from one of the filters shown in FIG. 3, according to one embodiment of the present invention.

As can be seen from FIG. 4, many oscillations exist in the filtered signals, so that there are many zero and near-zero samples in the buffer. In order to remove these effects, an additional envelope filter may optionally be applied to the data in order to remove the localized zeros and non-zeros. FIG. 4 illustrates the effects and the optional envelope filtering step 405 on the oscillating output 402 of the CLAS1 filter 306".

At buffering step 204, each stream of filtered ECG signal data is segmented into sequential time segments, i.e. buffers ECG1 ECG2 . . . ECGi. One preferred arrangement is non-overlapped adjoining buffers of 3.5 seconds length. One sampling rate is 250 samples per second, which equates to 875 samples of ECG per buffer. Time segment length and sampling rates are predetermined, and may differ within the scope of the invention. Each of the data points from each buffer has a value, depending on the input and the underlying filter. An example of a filtered ECG buffer data set for CLAS1 is shown in FIG. 4.

It is preferred and advantageous that the buffering step 204 occurs after the filtering step 206. By filtering prior to buffering, the method avoids filter transients at the edge of each buffer. Otherwise, the method would require longer, overlapping buffers which would entail longer analyzing time with the attendant dilatory effects on patient outcomes.

At step 208, data in each of the filtered ECG buffers is compared to a threshold value. The number of data points falling within the threshold value for that filtered ECG buffer, called a score, is then calculated for use by the analyzing step 210. Of course, any mathematical equivalent to the number of data points, such as a proportion or a fraction, could be substituted within the scope of this method step. For the purposes of this illustration, the score for the filtered ECG buffer for the FLATS filter is designated the FLATS score. The score for the filtered ECG buffer for CLAS1 is designated the CLAS score. Accordingly, FIG. 2a illustrates that threshold comparisons step includes a threshold comparison for each of the parallel filtering steps, i.e. first through fourth parallel threshold comparison steps 208', 208'', 208''', and 208''''.

Threshold values for each of the filtered ECG buffer scores may be arrived at in a number of ways, the determinations of which fall within the scope of the present invention. Thresholds may be fixed, e.g. predetermined, or may be adaptive, e.g. are calculated based upon a mean value of all of the data points in the particular buffer. For example, the FLATS buffer data set may be scored against a fixed threshold value, and the CLAS buffer data set may be scored against an adaptive threshold value.

Figure 5:
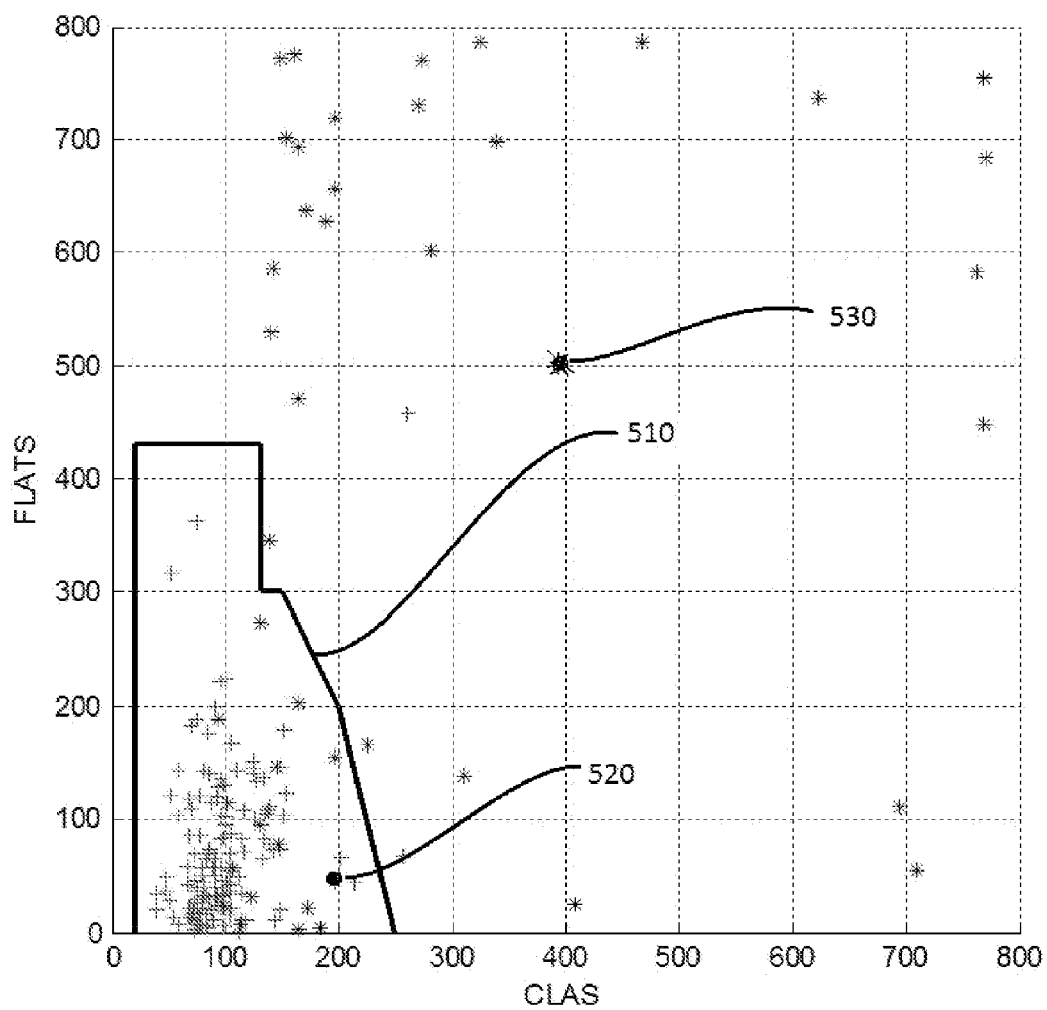
FIG. 5 illustrates an exemplary two-dimensional decision surface for classifying a corrupted ECG signal as VF or undecided, according to one embodiment of the invention.

The analyzing step 210 begins by comparing the filtered ECG buffer scores to a predetermined decision surface. The decision surface, which is constructed using databases of ECG signal data having CPR corruption noise, defines whether a given set of buffer scores indicates "VF" or "undecided", i.e. other than VF. One example of a decision surface in the CLAS and FLATS dimensions is illustrated in FIG. 5. In that example, decision surface 510 is constructed of corresponding pairs of one of the CLAS scores and FLATS scores. Score pairs that fall within the decision surface 510 indicate a VF condition. Score pairs that fall outside the decision surface 510 indicate an undecided condition. Additional dimensions of decision surface may be added using threshold values for additional filtered ECG buffers as desired to create a more accurate VF decision. Although only two dimensions are shown here, three or more dimensions may be used for a decision surface that incorporates the other CLAS scores as well.

Analyzing step 210 proceeds by comparing two or more buffer scores that represent the particular cardiac signal characteristics to the decision surface in order to determine VF or other than VF. For the example shown in FIG. 5, an example pair of CLAS/FLATS score is shown at 520, indicating VF. The value pair 530 that falls outside the decision surface 510, e.g. above and/or to the right, indicates an undecided, i.e. other than VF, condition.

Each original time-segmented ECG buffer can thus be designated as "shock advised", i.e. corresponding to VF, or "undecided", i.e. corresponding to "other than VF". Once the ECG buffer is determined as shock advised or undecided, ART repeats the steps of capturing, obtaining, filtering, and analyzing for the next ECG buffer in the time sequence as shown in "select next ECG buffer" step 212. The process of repeating enables additional methods of combining each new buffer with previous buffers to generate an overall continuous determination of the presence of VF or not.

The above-described method has been shown to identify VF with an accuracy that is sufficient to safely make a shock determination during the application of CPR, and without the need for further confirmation of the analysis during a "hands-off" time. The sensitivity of ART to VF for a single buffer of CPR-contaminated ECG has been demonstrated to exceed 70%, i.e. ART will detect true VF more than 70% of the occurrences. Similarly, the specificity of ART has been demonstrated to exceed 95% for a single buffer of ECG, i.e. will not generate a false positive VF indication from more than 95% of "other than VF" occurrences.

It may also be noted that the ART performance during "quiet" periods approaches that already demonstrated in the existing PAS algorithm. The sensitivity of ART to VF on ECG data that is not contaminated with CPR artifact exceeds 80%, as compared to PAS on similar data at about 94%. Specificity of ART and PAS to false VF on a buffer of "clean" ECG is nearly identical.

Figure 2B:
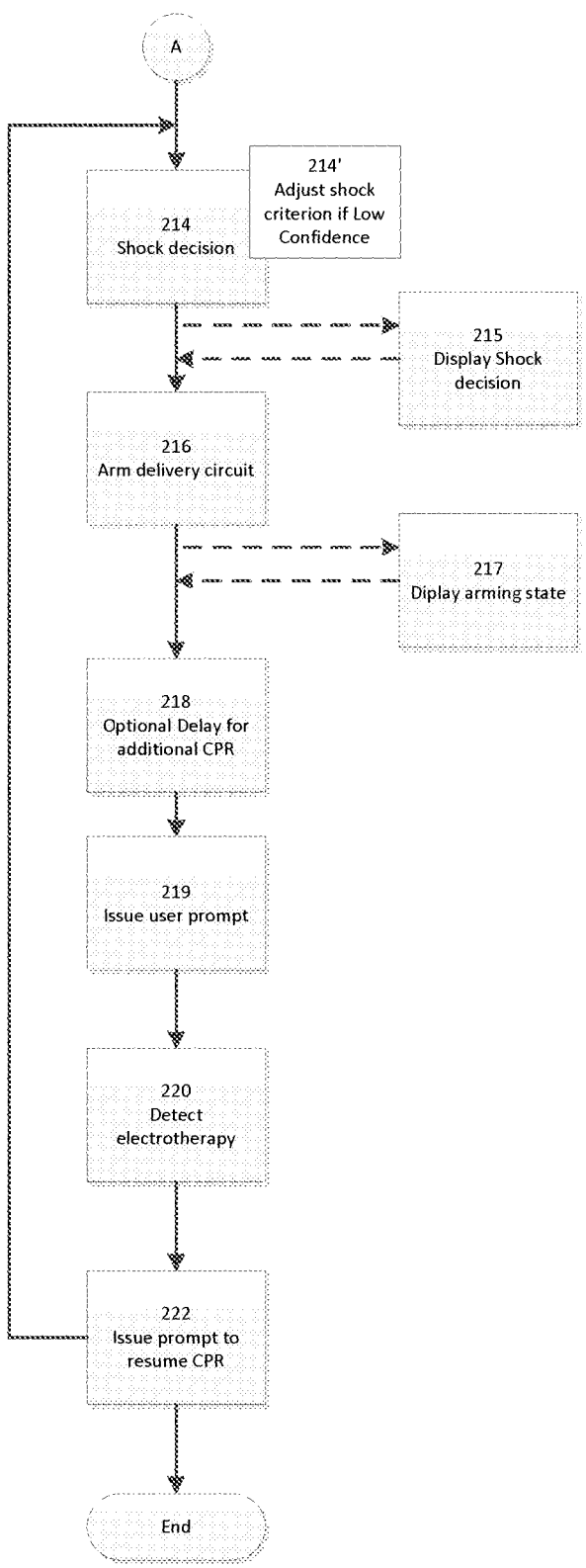
FIG. 2b illustrates a process flow for determining a shockable cardiac rhythm from the analyzed ECG, according to one embodiment of the present invention.

Now turning to FIG. 2b, the method continues. One preferred embodiment of the method comprises the aforedescribed steps 202-212 as being performed in a separate processor, such as a DSP, from the steps mentioned in the following several paragraphs. Such an arrangement allows each ECG buffer in turn to be analyzed and classified as VF or "undecided" relatively independently of the shock decision and control processor, which primarily needs only the stream of classifications data from the ECG signal stream. Another preferred embodiment of the method comprises further separation of processing into multiple components. For example, digitization of the ECG signal input at step 202 could be handled in a front end chip such as an ASIC, the digital stream fed into a DSP for filtering the digitized ECG signal stream into the separate filtered streams corresponding to method step 206. Yet another processor would then receive the filtered streams for final classification, decision-making, and response handling functions that will be described in the following paragraphs.

If VF is determined from the ECG buffer at analyzing step 210, i.e. a "shock advised" outcome, then the underlying ECG rhythm is generally assumed be a shockable cardiac rhythm. But the optimal response to a VF determination may not simply be to prepare the underlying device to provide electrotherapy. Instead, it may be preferable to obtain confirming determinations, or to otherwise to convey the determination to the user in some manner that does not unduly disrupt the ongoing cardiac rescue. A separate deciding step 214 is thus warranted for these purposes, and is shown in FIG. 2*b* as taking input from analyzing step 210. Examples of such situations will be provided in following paragraphs.

Because ART sequentially analyzes multiple ECG buffers during a minutes-long CPR period, accumulated sensitivity to an ongoing patient condition of VF will increase, i.e. more chances to detect a true VF condition. But it is also expected that accumulated specificity will decrease, i.e. more chances to mistake an "undecided" condition as VF. In order to maintain the specificity of the overall method at an acceptable level over this relatively long period of time, optional multiple-buffer rules may be developed for making a shock decision from VF/undecided decisions over time-consecutive ECG data buffers. The repeated, second analyzing step 210 of an ECG buffer of a later, second predetermined time segment is provided to the deciding step 214. Deciding step 214 then additionally bases its final decision on the second analyzing step.

For example, the analyzing step 210 may determine that a cardiac rhythm is shockable only if three time-consecutive ECG buffers indicate VF. Otherwise, the analyzing step indicates a non-shockable rhythm. It has been shown that, under these rules, ART maintains a specificity of >95% over long periods of CPR, while sensitivity remains >70%. In some cases, sensitivity can exceed 95% and specificity can exceed 98%. Such performance is acceptable for making shock decisions during CPR periods. In summary, whereas deciding step 214 essentially receives an ongoing stream of VF/undecided ECG buffer, the step 214 applies the rules for the final decision that the underlying device should operably proceed to the delivery of a defibrillating shock.

A displaying step 215 may be initiated immediately upon the determination, such as a visual graphic or textual message on a display, a light signal, or a subtle audible signal. Preferably, the displaying step 215 is provided even before the device is fully prepared to deliver electrotherapy, but in an unobtrusive manner that does not distract the user from continuing CPR compressions up until the device is ready for shock delivery. On the other hand, there are some modes of operation in which it may be preferable not to provide any information at all to the user of a shock determination until arming is complete. Some lay users may be unnecessarily distracted or startled from providing CPR compressions at the mere indication that the device is preparing to deliver a shock.

Figure 7:
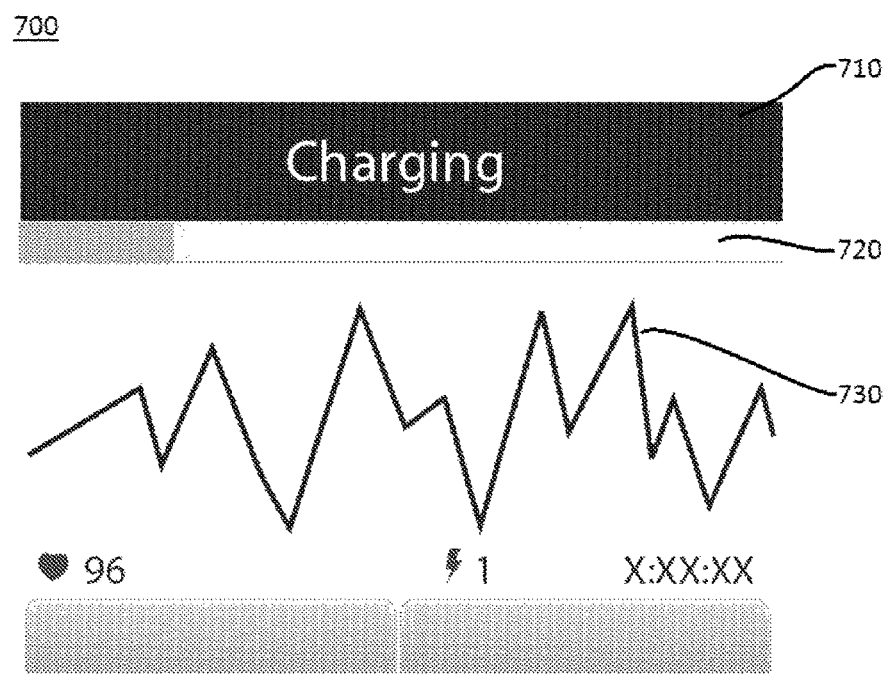
FIG. 7 illustrates an exemplary visual display that indicates the charging state of the device, according to the present invention.

Responsive to a determination from deciding step 214 that a shockable cardiac rhythm exists and that electrotherapy should be provided, an arming step 216 begins. Arming step 216 may consist of charging a high voltage charging circuit with sufficient energy to defibrillate a patient. Arming step 216 may include an audible and/or visual indicator that the arming step has begun, along with some indication as to the progress toward being fully prepared for shock delivery, step 217. For example, dynamic bar graph indicia 720 on a visual display 700 may show the progressive filling of a bar graph corresponding to the increasing charge state of the high voltage circuit. A text message 710 on display 700 may also indicate that charging is ongoing. An ECG display 730 may be displayed on the charging state display simultaneously with the progress indicators. FIG. 7 illustrates one exemplary embodiment of such a display 700. An audible progress indicator could comprise a continuous tone of rising frequency which stops when a fully charged state is attained.

At the completion of arming step 216, the electrotherapy device is fully prepared to deliver a shock. After arming, it is preferable that a step of automatically issuing a user prompt 219 to stop CPR for the delivery of electrotherapy occurs. An audible prompt from a speaker 830, an illuminated or flashing shock button light 820, and/or a display indication 802 may be used to signal the user to stop CPR for shock delivery. See FIG. 8 for an example of these indicators on a user interface 818. In the case of an AED, the prompt may also instruct the user to press the shock button 892 to deliver a shock. In the case of a fully automatic defibrillator, a shock may automatically be delivered immediately after the prompt occurs, still at step 219. If the user is employing electrically insulated gloves or other such protective gear, any prompting to "stop CPR" at step 219 may optionally be omitted altogether.

In some circumstances, it may be desirable to delay the issuing of the user prompt to stop CPR at step 219 until a minimum amount of CPR has been provided. For example, it may be desirable to conduct at least 30 seconds of uninterrupted CPR prior to delivering a shock. Optional delay step 218 may be incorporated to the inventive method in order to ensure such a minimum CPR time.

Immediately after the delivery of electrotherapy, the user may be automatically prompted to resume CPR at step 222. The device may optionally be enabled to detect the delivery of electrotherapy, at step 220. Detecting delivery can be obtained by sensing outgoing current, a button press, or the like. Then the method process returns to the steps of capturing, obtaining, filtering, and analyzing in accordance with the state of the cardiac rescue.

The method steps described above allow CPR to continue right up until the moment of delivering electrotherapy, and then to resume CPR immediately thereafter. The result is that the proportion of "hands-on" time during a cardiac rescue is increased, thereby improving the effectiveness of the overall treatment. Idle time waiting for a "hands-off" ECG analysis can be essentially eliminated, thereby avoiding the loss of blood pressure and flow that occurs so quickly upon cessation of CPR. These benefits can be realized along with the method's ability to treat a reversion to VF during the CPR period. If refibrillation occurs, the method simply detects the VF and prepares for electrotherapy in the midst of the ongoing CPR compressions.

Other advantages are afforded by the inventive method. The inventors have discovered that the use of filters instead of wavelets somewhat reduces the computational load required to analyze for VF, and more effectively suppresses interference by power line noises or similar high-frequency noises. Most of the method steps can thus be accomplished in a single digital signal processor (DSP) that is arranged to receive the ECG signal stream, to process the stream, and then to output a continuous, time aligned and transformed ECG data stream. The DSP can also operate in parallel with a second processor that controls the final shock decision and delivery sequence in the AED. Also, the series of filters can be easily adjusted to also provide more robust rejection of signals induced by DC offsets, 50 Hz and 60 Hz external power-line noise.

Figure 6:
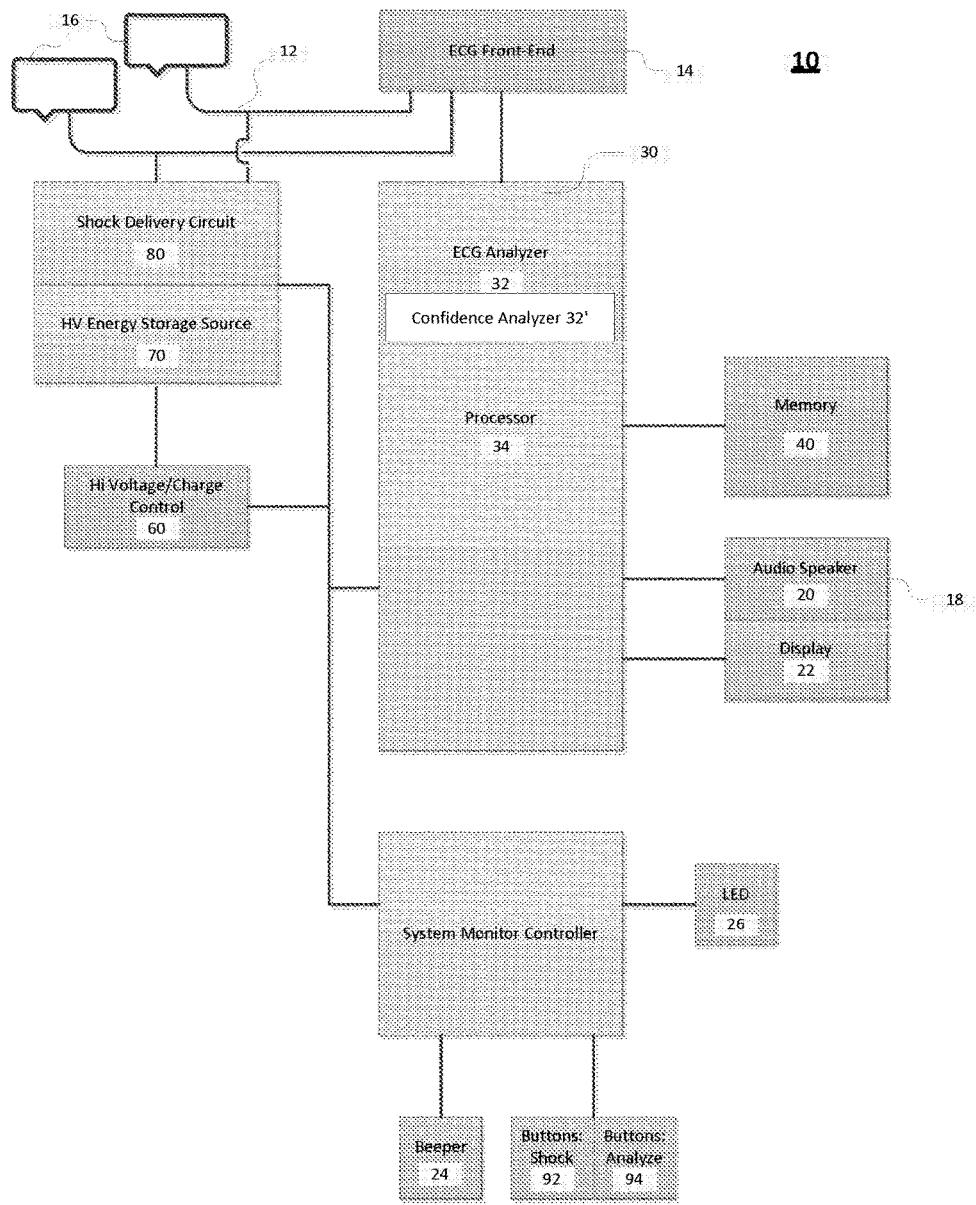
FIG. 6 illustrates a functional block diagram of an external defibrillator according to the present invention.

The afore-described method can be implemented in a medical device such as an external defibrillator. FIG. 6 is a functional block diagram of an external defibrillator 10 according to the one embodiment of the present invention. Defibrillator 10 is configured as an AED that is intended for use during a cardiac rescue which includes CPR. It is designed for small physical size, light weight, and relatively simple user interface capable of being operated by personnel without high training levels or who otherwise would use the defibrillator 10 only infrequently. Although the present embodiment of the invention is described with respect to application in an AED, other embodiments include application in different types of defibrillators, for example, manual defibrillators, fully automatic defibrillators, and paramedic or clinical defibrillator/monitors.

Defibrillator 10 receives an input 12 of an ECG signal from, for example, two or more electrodes 16 that are connected to a patient. An ECG front end circuit 14 is in electrical communication with the input 12 via a connector plug and socket or the like. The ECG front end circuit 14 operates to amplify, buffer, filter and optionally digitize an electrical ECG signal generated by the patient's heart to produce a stream of digitized ECG samples. The digitized ECG samples are provided to a controller 30, which may be a processor that combines a DSP and ARM processor. One exemplary controller is the family of Applications Processors manufactured by Texas Instruments Incorporated Inc. In one embodiment of the apparatus, the DSP conducts all of the previously described filtering under the ART protocol, and then passes the multiple streams of filtered ECG data to the ARM processor. The ARM buffers the stream of digitized ECG signal data into segments (buffers) corresponding to a predetermined time. The ARM performs an outcomes analysis on the filtered ECG data to detect VF, shockable VT or other shockable rhythms. In accordance with the present invention, the ARM uses the outcomes analysis to determine a treatment regimen which is most beneficial to the patient. These controller 30 portions of the DSP and ARM thus operate together as an ECG analyzer 32 as described in the above method steps 202 through 222. Of course, the scope of the present invention is not limited to a particular DSP/ARM configuration. The foregoing and following functions may be equivalently implemented in a single processor or distributed among multiple processors.

ECG analyzer 32 incorporates an analysis algorithm that can determine a shockable rhythm in the presence of CPR-related signal noise artifact with a sensitivity of greater than about 70% and a specificity of greater than about 95%. The accuracy of the ECG analyzer is sufficient to safely and effectively assess the cardiac state of the input signal in the presence of CPR compressions noise. One such analysis algorithm is ART as described previously.

If ECG analyzer 32 determines a shockable rhythm in combination with the determination of a treatment regimen that indicates the need for a defibrillation shock, then processor 34, responsive to the output of ECG analyzer 32, sends a signal to a HV (high voltage) charging circuit 60 to charge a HV energy storage source 70 in preparation for delivering a shock. When the HV energy storage source 70 is fully charged, processor 34 directs a shock button 92 on a user interface 818, FIG. 8, to begin flashing to re-direct the attention of the user from the task of providing CPR compressions to the task of delivering electrotherapy.

As will be described in more detail, processor 34 can initiate the preparation for a defibrillating shock immediately upon detection of a shockable cardiac rhythm, i.e. in a continuous mode of operation, and issue instructions to interrupt of CPR compressions for electrotherapy as soon as the device is armed. Alternatively, the processor 34 can initiate preparation for a defibrillating shock prior to the end of a predetermined period of CPR compressions, and can instruct the immediate delivery of electrotherapy simultaneously with the end of the predetermined period. This last mode is called a scheduled mode.

In either continuous or scheduled mode, processor 34 controls the user interface 18 to issue aural prompts to stop CPR and press the shock button to deliver a defibrillating shock. These prompts should be issued together and in quick order so that delay between stopping CPR and pressing the shock button is minimized. The user interface 18 should similarly issue an aural prompt via audio speaker 20 to resume CPR as soon as possible after the processor 34 senses that a defibrillating shock has been delivered, e.g. by sensing the button press, current flow from the HV storage circuit, etc. corresponding visual prompts may be issued simultaneously with the aural prompts.

When the user presses the shock button 92 on the user interface 818, a defibrillation shock is delivered from HV energy storage source 70 through a shock delivery circuit 80. In a preferred embodiment, shock delivery circuit 80 is electrically connected via an output of the AED to the same electrodes 16 which receive the raw ECG signal.

Processor 34 also provides control of the user interface (UI) output functions in the device. The user interface 18 is the primary means for guiding the user through the progress of the cardiac rescue protocol, and so includes at least one of an aural instruction output and a visual display. In particular, user interface 18 may comprise an audio speaker 20 to issue an aural verbal or signal prompt to the user regarding a state of the rescue, an instruction as to a next step to be taken in the rescue, or regarding instructions responsive the determined shockable cardiac rhythm. User interface 18 may also convey audible information via a beeper 24. User interface 18 may also provide visual text or graphical indications on a display 22. User interface 18 may also convey visual information via flashing light LED 26, which may illuminate adjacent graphics or buttons to be pressed. Preferably, processor 34 controls the user interface such that each of these cues is provided in a manner that optimizes the desired response of the user. Audible and visual cues pertaining to the same information need not be issued simultaneously if one or the other cue may detract from the desired response. For example, processor 34 may control the charging circuit to fully charge the HV storage source to the armed state prior to issuing any instructions at all. Alternatively, processor 34 may drive the user interface to indicate a determination of a shockable cardiac rhythm on visual display 22 prior to issuing related aural instructions on speaker 20. And again with reference to FIG. 7, processor 34 may drive the user interface to indicate the state of the HV charging circuit prior to issuing related aural instructions on speaker 20.

Software instructions for operating controller 30 are disposed in an onboard memory 40. Instructions in non-volatile memory may include the algorithm for the ART algorithm, the algorithm for PAS, instructions for a CPR rescue protocol that includes a period for providing CPR compressions, UI configurations for multiple user types, and the like. Volatile memory may include software-embodied records of device self-tests, device operating data, and rescue event audio and visual recordings.

Other optional features of the defibrillator shown in FIG. 6 include a System Monitor Controller which receives signals from various Buttons (e.g. Power On, Shock) and provides signals for the beeper and LED lights. State changes of the buttons and sensors are transmitted back to the processor 34 through a communications interface. This feature enables very low-power standby operations with wake-up sensing by means of the button actuation and readiness status outputs.

Figure 8:
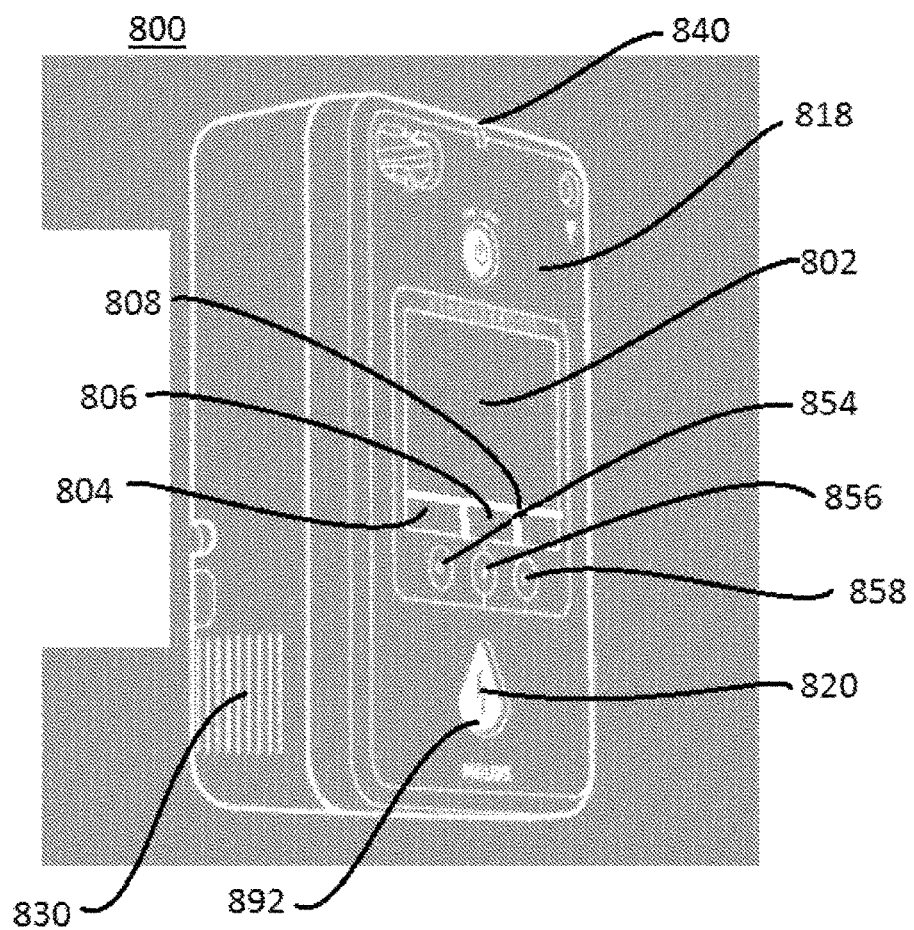
FIG. 8 illustrates a user interface on the external surface of an AED, according to one embodiment of the present invention.

FIG. 8 illustrates a structural embodiment of a user interface 818 on the exterior surfaces of an AED 800 which corresponds generally to the user interface 18 of the FIG. 6 functional block diagram. User interface 818 may include a visual display 802 which provides graphic and textual information pertaining to the state of the cardiac rescue. User interface 818 may also include a speaker 830 which issues aural and audible prompts. An LED 840 may provide a light-based signal for readiness or malfunction. User interface 818 may also include first, second and third configurable buttons 854, 856, 858 whose function changes depending on the state of the rescue or on the configuration of the device. The configurable buttons functions may further be indicated by contextual labels 804, 806, 808 displayed on visual display 802. For example, if the device is configured for an advanced operating mode, display 802 may indicate that an adjacent configurable button 854 is configured as an "analyze" button 94. Analyze button 94 may operate to truncate an ongoing rescue protocol. Truncation immediately ceases a CPR period and prepares the defibrillator for immediate delivery of electrotherapy. Embodiments of the analyze button 94 and its functionality will be described in more detail below.

The preferred embodiment of the invention comprises the defibrillator 10 that operates in a CPR rescue protocol, the operation characterized in that apparatus-caused delay between providing CPR compressions and delivering electrotherapy is eliminated. In order to achieve this result, the ECG analysis algorithm as described above is incorporated which can accurately determine a shockable cardiac rhythm, without undue false alerting, even in the presence of motion-related signal noise induced by CPR compressions. ART is such an algorithm. ART allows the background detection of a shockable cardiac rhythm, the charging of the HV storage circuit and the arming of the device while CPR compressions are being applied. The defibrillator is then ready to deliver a shock simultaneously with the cessation of CPR compressions.

Modes of Operation Enabled by the Inventive Method and Apparatus

The defibrillator as described above can be configured with any of several different modes of operation. The novel modes of operation are made possible as a result of the inventive analysis method. The modes of operation address various new issues which may arise under the adoption of the inventive method in the inventive apparatus.

Each mode of operation may be pre-loaded into the defibrillator memory 40. An administrator or user of the device can select the desired mode during device setup prior to the cardiac rescue. The particular mode is selected according to local rescue protocols and/or preference of the medical director for that locality.

The Continuous CPR Mode of Operation

Figure 9:
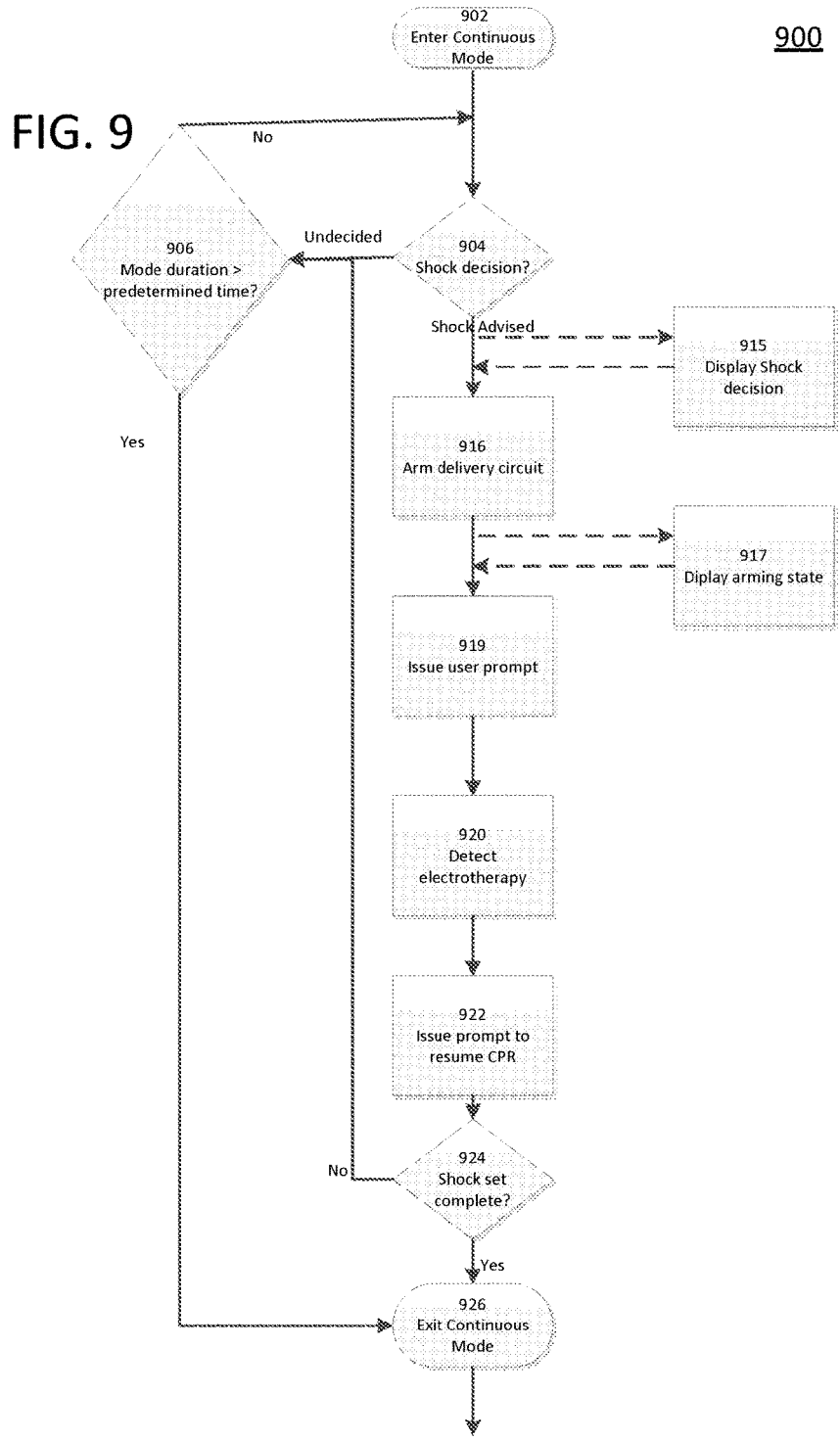
FIG. 9 illustrates a process flow for illustrating a continuous CPR rescue mode of operation, according to one embodiment of the invention.

FIG. 9 illustrates one embodiment of a continuous CPR rescue mode of operation 900. When the defibrillator is configured in a continuous mode, its processor always initiates a defibrillating shock whenever ART detects VF and the processor makes a shock decision. In the context of the following description, the term "continuous" is deemed to mean the immediate application of defibrillation therapy whenever a shockable rhythm is detected. This particular mode of operation may also be referred to as "Analysis through CPR custom" mode.

Continuous CPR rescue mode of operation is entered at step 902, where the ART algorithm has begun to evaluate the stream of ECG buffers. CPR compressions may be ongoing at this time, but are not necessary to the mode. The processor determines a shock decision at step 904, and if it determines a "shock advised" condition, the processor begins to prepare the defibrillator to deliver electrotherapy. Accordingly, the method proceeds similarly to that described at FIG. 2b steps 215 through 222.

A shock advised displaying step 915 may be initiated immediately upon the determination, such as with a visual graphic or textual message on a display, a light signal, or a subtle audible signal. Preferably, the shock advised displaying step 915 is provided even before the device is fully prepared to deliver electrotherapy, but in an unobtrusive manner that does not distract the user from continuing CPR compressions up until the device is ready for shock delivery. On the other hand, there are some modes of operation in which it may be preferable not to provide any information at all to the user of a shock determination until arming is complete. Some lay users may be unnecessarily distracted or startled from providing CPR compressions at the mere indication that the device is preparing to deliver a shock.

Responsive to a determination from deciding step 904 that a shockable cardiac rhythm exists and that electrotherapy should be provided, an arming step 916 begins. Arming step 916 may consist of charging a high voltage charging circuit with sufficient energy to defibrillate a patient. Arming step 916 may include an audible and/or visual indicator that the arming step has begun, along with some indication as to the progress toward being fully prepared for shock delivery, at arming progress displaying step 917. For example, dynamic bar graph indicia 720 on a visual display 700 may show the progressive filling of a bar graph corresponding to the increasing charge state of the high voltage circuit. A text message 710 on display 700 may also indicate that charging is ongoing. An ECG display 730 may be displayed on the charging state display simultaneously with the progress indicators. FIG. 7 illustrates one exemplary embodiment of such a display 700.

At the completion of arming step 916, the electrotherapy device is fully prepared to deliver a shock. It is preferable that, immediately after arming is complete, a step of automatically issuing a user prompt 919 to stop CPR for the delivery of electrotherapy occurs. An audible prompt from a speaker 830, an illuminated or flashing shock button light 820, and/or a display indication 802 may be used to signal the user to stop CPR for immediate shock delivery. See FIG. 8 for an example of these indicators on a user interface 818. In the case of an AED, the prompt may also instruct the user to press the shock button 892 to deliver a shock. In the case of a fully automatic defibrillator, a shock may automatically be delivered immediately after the prompt occurs, still at step 919. The fully automatic AED may use methods such as electrode impedance monitoring or using the analysis algorithm to determine an absence of CPR-related signal noise artifact to determine when the operator is not touching the patient, and automatically deliver the shock accordingly. If the user is employing electrically insulated gloves or other such protective gear, any prompting to "stop CPR" at step 919 may optionally be omitted altogether.

Immediately after the delivery of electrotherapy, the user should be immediately prompted to resume CPR at step 922 in order to minimize hands-off time. The device may optionally be enabled to detect the delivery of electrotherapy, at step 920. Detecting delivery can be obtained by sensing outgoing current, a button press, or the like.

An optional step 924 of checking for the completion of a shock set may be performed after step 922 and prior to returning to the shock deciding step 904. A shock set is a predetermined number of electrotherapeutic shocks delivered within one period of continuous CPR rescue mode of operation. The predetermined number may be set by a medical administrator according to local preferences. A preferred number of shocks in a shock set is three.

If the shock set completion checking step 924 determines that the shock set is complete, then the method exits the continuous CPR rescue mode of operation at exit step 926. Otherwise, the method proceeds to continuous mode end decision step 906.

Decision step 906 determines whether the duration of the continuous mode of operation has reached a predetermined time. Predetermined times may be one minute or two minutes, or may be set at other desired times by a medical administrator according to local preferences. If the time has been reached, the method exits the continuous mode at exit step 926. Otherwise, the method returns to the shock deciding step 904 for continued analysis of the next ECG buffer(s). The loop will continue until one of a shock set is complete or the continuous mode period is complete.

If a patient is responsive to electrotherapy, or never needs it at all, the AED operating in continuous mode will quietly analyze in the background while periodically providing appropriate guidance to check the patient or to continue CPR. The AED shock delivery circuit will never unnecessarily be charged, thus saving battery power and extending the operating time. This mode may be particularly beneficial during use in commercial aircraft, where very-long-duration cardiac rescues are sometimes experienced during flight.

Figure 12:
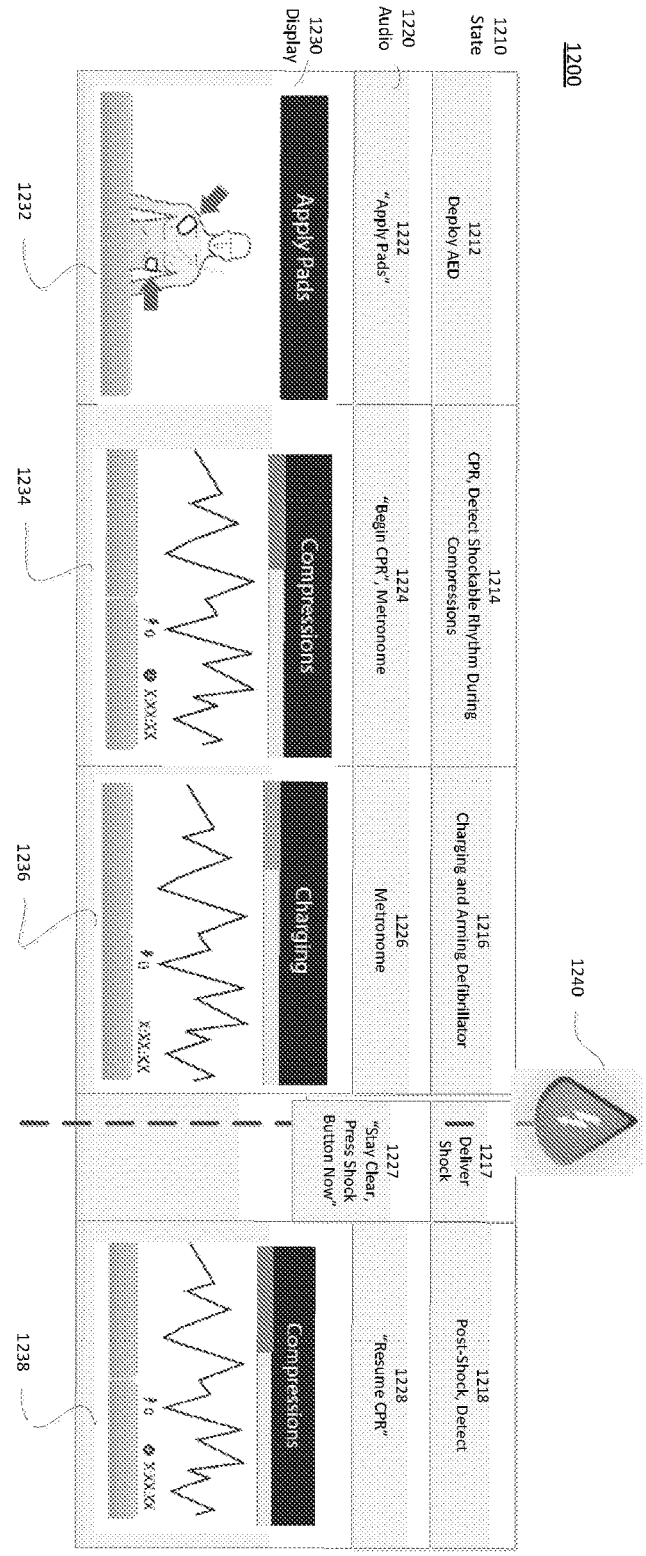
FIG. 12 illustrates a timeline view of audio and visual information that provided during a cardiac rescue in the continuous CPR rescue mode of operation.

FIG. 12 provides an illustration of the informational outputs provided during the continuous CPR rescue mode of operation. Time line 1200 includes three rows along a horizontal axis representing the time in the cardiac rescue. The top row 1210 indicates the current state of the device. The middle row 1220 indicates the audible prompts that are issued by the device at the current state. The bottom row 1230 indicates the displays that are shown on the device user interface at the current state.

At the beginning of the rescue at deployment state 1212, electrodes may not yet be deployed. An audible prompt 1222 and a visual display 1232 to "apply pads" are preferably provided simultaneously at this state in order to emphatically instruct the user to perform this necessary action.

After the electrodes are deployed, the device will sense that it is receiving ECG signals, and will enter the "analyzing during CPR" state 1214. At this state, audio instructions and timing signals 1224 along with optional display information 1234 are provided to assist the user in providing effective CPR. During this time, the ECG analyzer and shock determination processor are operating.

If the device detects a shockable cardiac rhythm, the state enters the charging and arming state 1216. Unlike prior art devices, however, the inventive device provides no, or only subtle, audible warning that a shock is advised and that the device is preparing itself to deliver therapy. Instead, CPR-related instructions at CPR state 1226 continue. This feature is particularly useful for the lay user having little prior experience with a cardiac rescue. By refraining from audible prompts that a shock is advised, the device forestalls the lay user, who may be concerned about being shocked, from stopping CPR compressions prematurely. An unobtrusive display message may instead be provided at charging display state 1236 to indicate a charging state. As can be seen in FIG. 12, the ongoing CPR and device charging state may be displayed there either textually or graphically or in some combination.

Only when the device is armed and ready to deliver a shock at state 1217 is an audible prompt issued to the user at the "deliver shock" audible prompt 1227. Simultaneously with the prompt, the shock button illuminates or flashes at state 1240 to attract the user's attention to press the button. An audible instruction such as "stay clear of the patient, press the shock button now" is conveyed at this state.

After the shock button is pressed at state 1217, the rescue is immediately resumed at a post-shock state 1218. An audible prompt to "resume CPR" 1228 is issued as soon as practicable after shock delivery, along with an appropriate display at 1238 which instructs the user to resume compressions. The rescue then loops back to state 1214 until or if another shockable rhythm is detected.

The Scheduled Mode of Operation

The scheduled CPR mode of operation appears familiar to a user of a prior art AED, but it actually functions in a significantly different way. Unlike in the prior art AEDs, an AED functioning in a scheduled CPR mode of operation is analyzing the ECG even during CPR. But in this scheduled CPR mode of operation, the AED refrains from issuing prompts to discontinue CPR regardless of the underlying sensed cardiac rhythm. Only after a predetermined and uninterrupted period of CPR has occurred does the device prompt the user to stop CPR and deliver a shock. The AED immediately, or at an appropriate time prior to the end of the period, prepares the device for electrotherapy upon a shockable rhythm detection such that the device is ready to deliver a shock simultaneously with the end of the fixed period. This preparation preferably occurs in the background in order to reduce noise and confusion during CPR compressions. In the context of the following description, the term "scheduled" can be deemed to mean the deferred application of defibrillation therapy to the end of a predetermined period even if a shockable rhythm is detected during the period. This mode is also referred to as "Analysis through CPR On."

Figure 10:
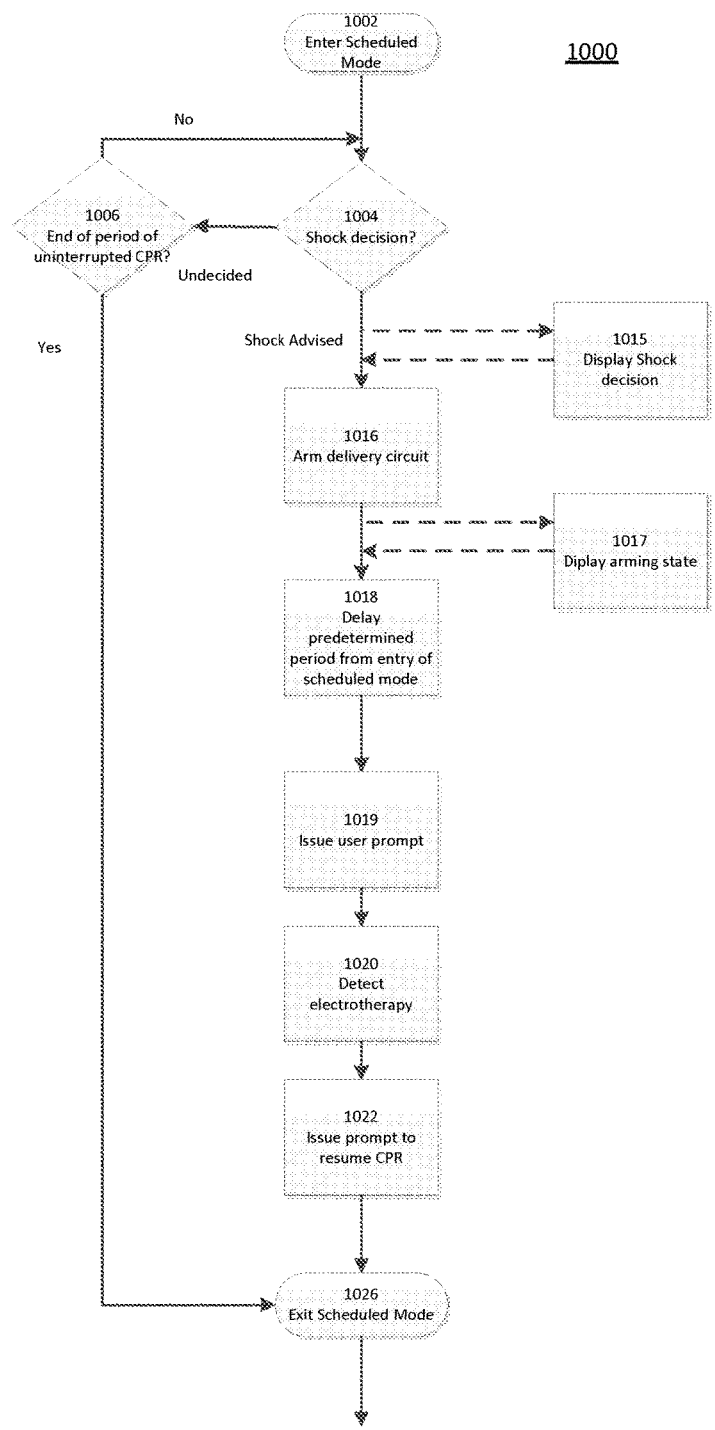
FIG. 10 illustrates a process flow for illustrating a scheduled CPR rescue mode of operation, according to one embodiment of the invention.

FIG. 10 illustrates one embodiment of a scheduled CPR rescue mode of operation 1000. When the defibrillator is configured in a scheduled mode, its processor delays the initiation of a defibrillating shock after ART detects VF and the processor makes a shock decision. The arming of the device for delivering electrotherapy is delayed until near the end of a predetermined period of uninterruptible CPR.

Scheduled CPR rescue mode of operation is entered at step 1002, where the ART algorithm has begun to evaluate a stream of ECG buffers as previously described. The AED may be providing via the user interface visual and aural user prompts to apply CPR compressions at this time, but this initial condition is not necessary to the mode.

The ART evaluations of ECG buffers may be distinguished from shock decisions that are made from them. For example, in this scheduled CPR rescue mode, individual ECG buffer evaluations of "undecided" or "shock advised" at step 1002 may be disregarded for therapy delivery purposes until the last portion of the scheduled mode period. Alternatively, these evaluations may be accumulated and used later in the period for decision-making.

The processor determines a shock decision at step 1004. If step 1004 determines a "shock advised" condition, the processor begins the process of preparing the defibrillator to deliver electrotherapy.

A shock advised displaying step 1015 may be initiated immediately upon the determination, such as with a visual graphic or textual message on a display, a light signal, or a very subtle audible signal. Preferably, the shock advised displaying step 1015 is provided even before the device is fully prepared to deliver electrotherapy, but in an unobtrusive manner that does not distract the user from continuing CPR compressions up until the device is ready for shock delivery. On the other hand, there are some modes of operation in which it may be preferable not to provide any information at all to the user of a shock determination until arming is complete. This is because some lay users may be unnecessarily distracted or startled from providing CPR compressions at the mere indication that the device is preparing to deliver a shock.

Responsive to a determination from decision step 1004 that a shockable cardiac rhythm exists and that electrotherapy should be provided, an arming step 1016 begins. Arming step 1016 may consist of charging a high voltage charging circuit with sufficient energy to defibrillate a patient. Arming step 1016 may include an audible and/or visual indicator that the arming step has begun, along with some indication as to the progress toward being fully prepared for shock delivery, at arming progress displaying step 1017. For example, dynamic bar graph indicia 720 on a visual display 700 may show the progressive filling of a bar graph corresponding to the increasing charge state of the high voltage circuit. A text message 710 on display 700 may also indicate that charging is ongoing. An ECG display 730 may be displayed on the charging state display simultaneously with the progress indicators. FIG. 7 illustrates one exemplary embodiment of such a display 700.

It is noted that the initiation of arming step 1016 may be timed such that the device reaches a fully armed state near the end of the predetermined and uninterrupted period of CPR. This reduces the possibility of an inadvertent shock being given to a provider of CPR compressions. Regardless of when the arming begins, at the completion of arming step 1016 the electrotherapy device is fully prepared to deliver a shock, and at that time issues the instructions.

A delay step 1018 should be completed after arming. Delay step 1018 is a predetermined period of time from the entry of the scheduled mode that ensures that a full and uninterrupted period of CPR occurs before any possible delivery of electrotherapy. Predetermined times may be one minute or two minutes, or may be set at any desired time by a medical administrator according to local preferences. A preferred period of time is two minutes, but may be in the range of from thirty (30) seconds or longer.

After delay step 1018 is complete, a step of automatically issuing a user prompt 1019 to stop CPR for the delivery of electrotherapy occurs. An audible prompt from a speaker 830, an illuminated or flashing shock button light 820, and/or a display indication 802 may be used to signal the user to stop CPR for shock delivery. See FIG. 8 for an example of these indicators on a user interface 818. In the case of an AED, the prompt may also instruct the user to press the shock button 892 to deliver a shock. In the case of a fully automatic defibrillator, a shock may automatically be delivered immediately after the prompt occurs, still at step 1019. If the user is employing electrically insulated gloves or other such protective gear, any prompting to "stop CPR" at step 1019 may optionally be omitted altogether.

Immediately after the delivery of electrotherapy, the user should be immediately prompted to resume CPR at step 1022 in order to minimize hands-off time. The device may optionally be enabled to detect the delivery of electrotherapy, at step 1020. Detecting delivery can be obtained by sensing outgoing current, a button press, or the like. Step 1020 may be employed to generate the resume prompt at step 1022. On the other hand, if step 1020 detects a lack of expected delivery of therapy, the device can respond by repeating the prompt, or by issuing a different prompt (not shown) that no shock has been delivered and that CPR should be resumed immediately. Then at step 1026, the method exits the scheduled CPR rescue mode of operation.

If the ART algorithm determines that the ECG is undecided, it continues to evaluate successive ECG buffers for a shock advised decision in the loop formed by decision step 1004 and an exit decision step 1006. Exit decision step 1006 merely determines whether the predetermined period of uninterrupted CPR is complete prior to returning to the analysis. If step 1006 determines that the period is complete, the method exits the scheduled CPR rescue mode of operation at step 1026. The predetermined period of uninterrupted CPR at step 1006 may be the same or a shorter duration than the period at step 1018.

By the above described method for scheduled mode and for a patient that is responsive to electrotherapy, or who never needs it at all, the AED operating in scheduled mode will quietly analyze in the background while periodically providing appropriate guidance to continue CPR. The AED shock delivery circuit will never unnecessarily be charged, thus saving battery power and extending the operating time. This mode also may be particularly beneficial during use in commercial aircraft.

Existing cardiac rescue protocols require at least a brief confirming analysis and a HV charging time after CPR is complete. Without the delay between CPR and shock that is necessary in the prior art devices, the scheduled mode AED provides more effective treatment. The steps of the scheduled mode of operation may be visualized as a repeated cycle of steps 214-222 in FIG. 2b with the analysis steps of FIG. 2a always occurring in the background. The issued user prompt step 219 is always delayed at delay step 218 until CPR compressions have been provided for a continuous and predetermined fixed period of time.

The AED in scheduled mode may be desirable to medical administrators who value a high proportion of uninterrupted CPR in a cardiac rescue as compared to treating a VF condition as rapidly as possible. The fixed period of CPR is also well known to responders, who value a consistent routine during rescues, e.g. swapping duties during the rescue to forestall fatigue. The consistent routine, however, comes at the cost of possible delaying electrotherapy to a refibrillating patient.

In scheduled mode, the AED may issue aural instructions and notifications differently than visual instructions in order to maintain the consistency and "flow" of a CPR routine. The AED may for example convey shock decisions and charging state only visually, so that a rescuer is not unnecessarily distracted by audible prompts which might include the distracting word "shock". As the end of the CPR period approaches, the AED may only then issue guidance that a shockable condition has been detected and that electrotherapy is ready for delivery. Then, at the end of the CPR period, the AED may issue aural and visual instructions to "stop CPR and deliver a shock now" while simultaneously flashing the shock button 892. The guidance process thus minimizes the human delay between the end of CPR and shocking.

Figure 13:
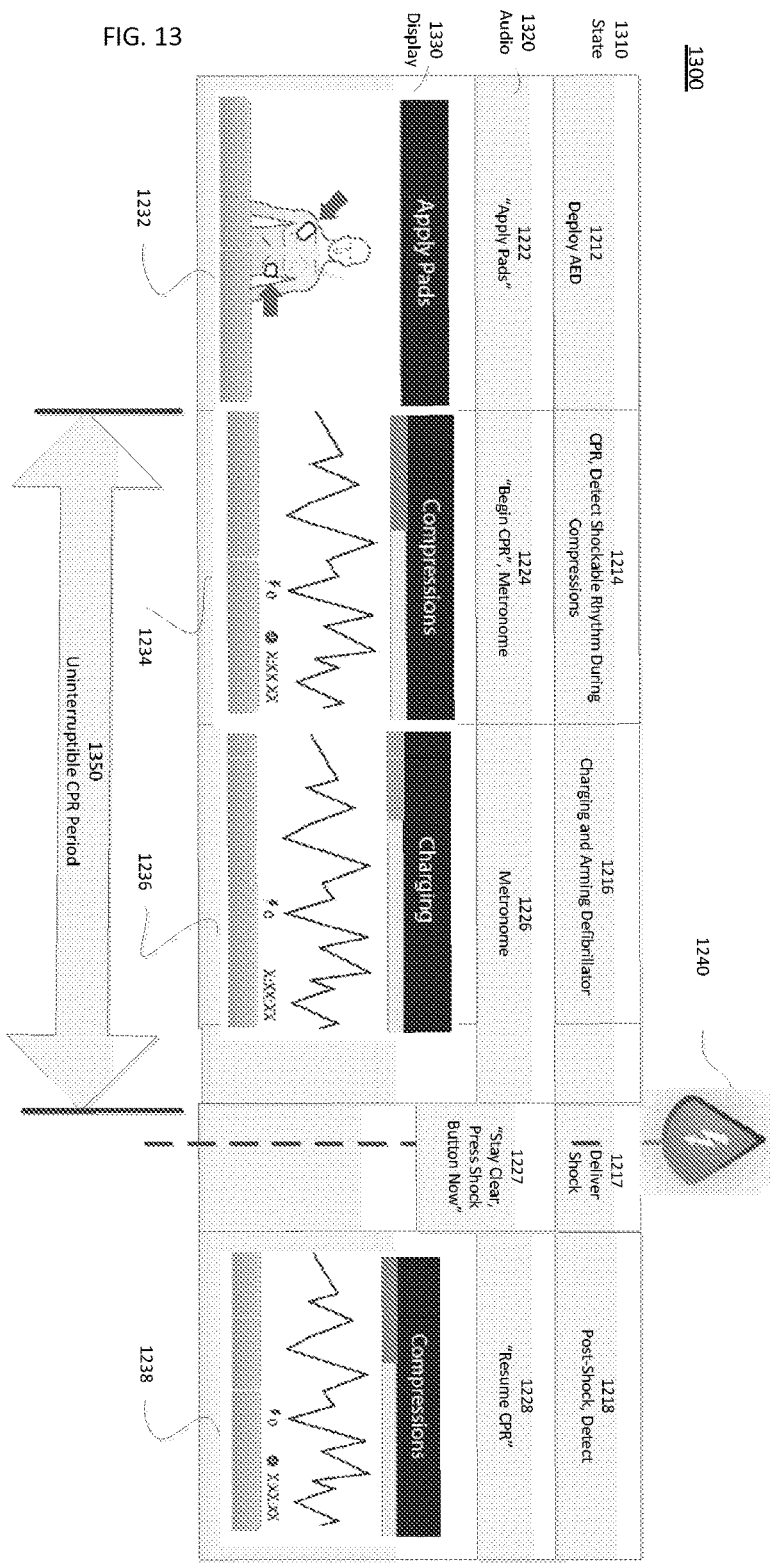
FIG. 13 illustrates a timeline view of audio and visual information that is provided during a cardiac rescue in the scheduled CPR rescue mode of operation.

FIG. 13 provides an illustration of the informational outputs provided during the scheduled CPR rescue mode of operation. Time line 1300 includes three rows along a horizontal axis representing the time in the cardiac rescue. The top row 1310 indicates the current state of the device. The middle row 1320 indicates the audible prompts that are issued by the device at the current state. The bottom row 1330 indicates the displays that are shown on the device user interface at the current state.

The rescue states and the audible and visual prompts in the scheduled CPR rescue mode of operation generally correspond to the similar elements described above at FIG. 12 for the continuous mode. But there is one significant difference that accords with the nature of the scheduled CPR rescue mode. If the device determines that a shock should be delivered and subsequently prepares for delivery in the charging and arming state 1216, no further audible or displayed prompts indicating that a shock should be delivered are provided until an uninterruptible CPR period 1350 has expired. The beginning of period 1350 coincides with the beginning of that session of CPR at state 1214 and may last a predetermined time, such as two minutes. Only after the uninterruptible CPR period 1350 has expired does the device begin to issue audible and visual prompts to deliver a shock at state 1217.

Combined Continuous Mode and Scheduled Mode with Shock Sets

The AED may also combine continuous mode and scheduled mode in a protocol that varies the proportion of electrotherapy opportunities relative to CPR compressions throughout the course of a cardiac rescue. The response of the patient to the protocol may influence a shift to a different mode of operation. For example, if a patient is not responsive to electrotherapy, an AED operating in continuous mode may not allow for enough uninterrupted CPR compressions time, so the AED may automatically shift to a scheduled mode instead. If a patient repeatedly experiences refibrillation, it may be desirable for the AED to maintain or revert to a continuous mode of operation to treat the condition more quickly.

Figure 11:
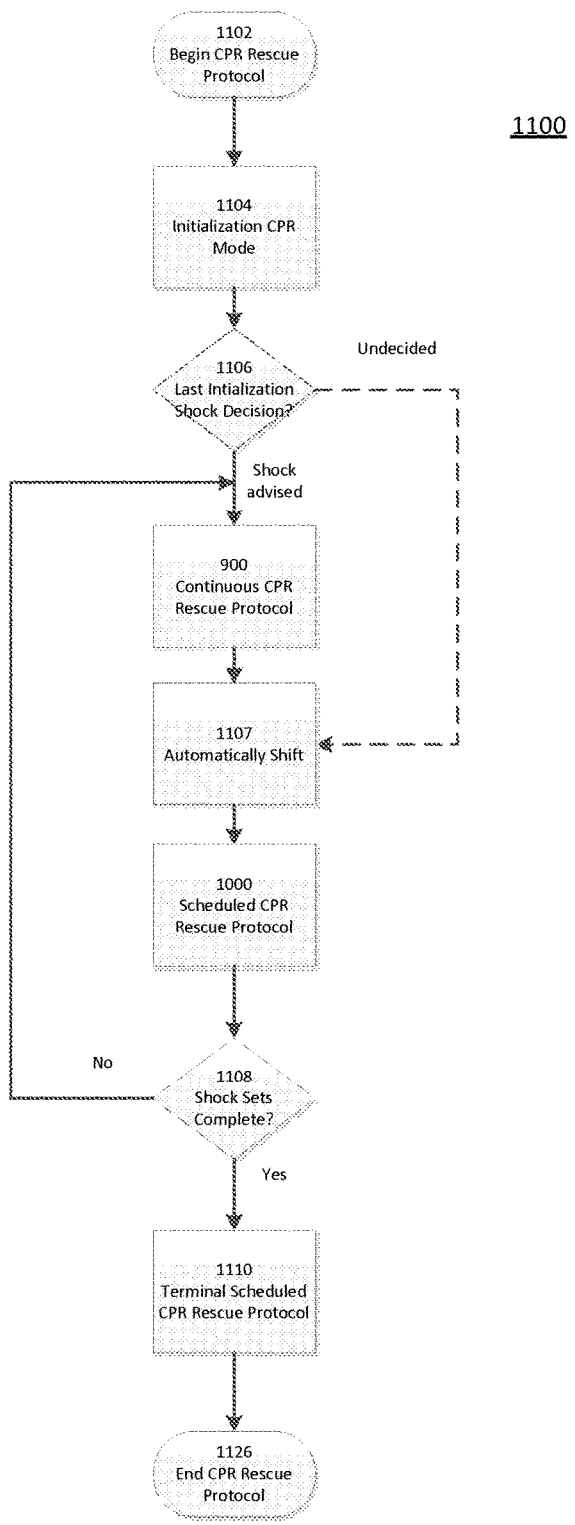
FIG. 11 illustrates a process flow for illustrating a cardiac rescue protocol which automatically shifts between a continuous and a scheduled CPR rescue mode of operation based on the progress of the rescue.

A combined CPR rescue protocol 1100 method of operation with shock sets is described in FIG. 11. The combined method for providing electrotherapy during the application of CPR includes a step 1107 of automatically shifting the protocol from a continuous CPR rescue protocol to a scheduled CPR rescue protocol following the completion of a predetermined number of shocks delivered during the continuous CPR rescue protocol. The predetermined group of shocks, all delivered within a single continuous CPR rescue protocol period, is called a shock set. The combined mode method may also include an automatic reversion from the scheduled to continuous mode after certain conditions are met.

The combined method begins at an entry step 1102, understood in general to include providing a defibrillator having two or more external electrodes, a processor, a user interface and a shock delivery circuit. Entry step 1102 begins when the device is deployed activated, and has its electrodes attached to a patient. The defibrillator may be one of a semi-automatic AED having a user-operated shock button, or may be a fully automatic AED having an automatic delivery of electrotherapy.

The AED may be configured to provide one of several startup protocols or operating modes when first activated at step 1102. The startup protocol may be a "shock first" protocol in which an ECG analysis is conducted immediately. If a shockable rhythm exists, the defibrillator arms itself for an immediate shock. After electrotherapy is delivered, the device proceeds with its rescue protocol. Alternatively, the startup protocol or operating mode may be "CPR First" which regardless of the underlying ECG rhythm, the AED guides the user through an initial period of uninterruptible CPR. This second CPR first startup protocol is shown at initialization CPR mode step 1104. At step 1104 a user prompt is automatically issued via the device user interface previously described to apply CPR compressions.

If the user properly follows the step 1104 prompts to apply CPR compressions, the ECG signal received by the device from the electrodes will be characterized by corruption from CPR compressions noise artifact. The afore-described algorithm such as ART analyzes this received ECG signal to decide whether a shockable cardiac rhythm exists.

Initialization step 1104 may optionally include a predetermined period of time, or an equivalent number of sensed compressions, before the device provides any guidance other than providing CPR compressions. A short initial period, such as between about 20 and 30 seconds or 30 compressions, is believed to be beneficial to some patients prior to delivery of any electrotherapy. Initialization step 1104 exits to an initial ECG shock decision step 1106.

Initial ECG shock decision step 1106 is also an optional step that is related to initialization step 1104. Step 1106 provides an initial shock decision which may determine which of a plurality of CPR rescue modes is to be used next. For example, if the initial shock decision at step 1106 is "undecided", then it may be preferable to begin a conventional fixed duration of CPR compressions before any further electrotherapy. This method step is indicated by the dashed line in FIG. 11 which proceeds to a scheduled CPR rescue protocol step 1000. But if the initial shock decision at step 1106 is "shock advised", then the method proceeds directly to a continuous CPR rescue protocol as indicated by step 900.

The combined method 1100 continues at step 900, wherein the device begins to operate in the continuous CPR rescue mode of operation. The method operates similarly to that previously described for the continuous mode, wherein responsive to a decision of a shockable cardiac rhythm in the analyzing step, the processor arms the shock delivery circuit for delivering electrotherapy and then immediately issues instructions via the user interface to stop CPR for the delivery. And as previously described, the continuous mode method step 900 automatically ends after the shock delivery circuit completes a predetermined electrotherapy shock set of a predetermined number of shocks delivered within that step 900. Alternatively and as previously described, step 900 ends if a lack of a determination of a shockable cardiac rhythm in the analyzing step persists for a predetermined time. The exit thus occurs responsive to the earlier of the predetermined time or after the shock delivery circuit delivers the predetermined number of electrotherapy shocks. And as previously described, an alternate exit may occur responsive to a sensed predetermined number of CPR compressions. At the exit, method 1100 automatically shifts at automatically shifting step 1107 from operating in the continuous mode to operating in a scheduled CPR rescue mode of operation at step 1000.

Method 1100 operates according to the scheduled mode of operation as described previously at step 1000. Here, responsive to a decision of a shockable cardiac rhythm in the analyzing step, the device processor arms the shock delivery circuit for delivering electrotherapy. After a predetermined period of uninterruptible CPR has passed, the processor issues instructions via the user interface to stop CPR for the delivery. After the predetermined period is complete, scheduled mode 1000 exits to completion of shock sets decision step 1108.

Method 1100 tracks the cumulative number of shock sets completed at previous step 900. It is noted that this number does not necessarily correspond to the number of times that continuous mode at step 900 has been entered or exited, because step 900 may exit due to the expiration of a predetermined time period instead of the completion of a shock set. If the exit is caused by expiration, for example, the shock counter within step 900 is reset. Thus each time continuous mode begins, another full shock set or expiration of the predetermined time is necessary for exit.

Completion of shock sets decision step 1108 controls whether or not method 1100 reverts to the continuous CPR rescue protocol after the exit from the scheduled CPR protocol. Reversion occurs unless a predetermined number of shock sets has been completed, which corresponds to the number of exits from continuous mode step 900 due to the completion of a shock set. If reversion occurs, steps 900 and 1000 are repeated. The cycle enabled by step 1108 repeats until the predetermined number of shock sets is completed. A preferred number of shock sets is three, and may range from one to seven.

This cycle between continuous and scheduled mode benefits those patients who require prompt electrotherapy early in a rescue, such as for refibrillating patients. But the cycle also enables the evolution to a cardiac rescue sequence which provides uninterruptible full CPR periods between shocks later in the sequence. Refibrillating patients that have not responded to prompt electrotherapy thus begin to receive full periods of CPR.

If the predetermined number of shock sets has been completed, discontinuing step 1108 will discontinue further reversions. The method instead proceeds to a terminal scheduled CPR rescue protocol at step 1110. At step 1110, all subsequent electrotherapy shocks will occur solely between intervals of uninterruptible CPR, i.e. after each predetermined period of uninterruptible CPR. When the CPR rescue is complete, the method 1100 ends by exiting at ending step 1126, which may be initiated by manually turning the device off at an on-off button.

Apparatus Interleaving the Continuous and Scheduled Methods

A device, such as the AED shown in FIGS. 6 and 8 above, may operate according to any of the afore described methods for interleaving CPR with electrotherapy. The AED is preferably controlled by processor 34 which is in communication with the ECG signal input 12, user interface 18, ECG analyzer 32, and memory 40 to provide instructional guidance to the user in the conduct of a cardiac rescue.

Processor 34 in particular operates the AED in a sequence of continuous CPR rescue mode of operation and the scheduled CPR rescue mode of operation that is more beneficial to the patient than prior art sequences. When operating in the continuous CPR rescue mode of operation and if the ECG analyzer decides a shockable cardiac rhythm, the processor arms the shock delivery circuit for delivering electrotherapy and then immediately issues instructions via the user interface to stop CPR for the delivery. The AED processor immediately issues instructions via the user interface to resume CPR as soon as it senses the delivery of electrotherapy in order to minimize "hands-off" time. When operating in the scheduled CPR rescue mode of operation and if the ECG analyzer decides a shockable cardiac rhythm, the processor arms the shock delivery circuit for delivering electrotherapy. This arming occurs either immediately upon the decision or alternatively starts charging in time to be fully armed at the end of the period. After a predetermined period of uninterruptible CPR, such as two minutes, the processor issues instructions via the user interface to stop CPR for the delivery.

Processor 34 is also responsive to the shock delivery circuit completing a predetermined electrotherapy shock set, after which the processor automatically shifts from the continuous CPR rescue mode of operation to the scheduled CPR rescue mode of operation.

The AED may be configured such that each electrotherapy shock set comprises a predetermined number of shocks delivered within a single instance of the continuous CPR rescue mode of operation. In one preferred embodiment, the AED may be programmable to set from two to five shocks in each shock set.

Processor 34 may further be operable to automatically revert the AED mode of operation from scheduled to continuous mode after one or more instances of scheduled CPR mode of operation. A sequence of modes that cycles between continuous and scheduled modes can thus be established. A preferred protocol is that the processor discontinues further reversions after the shock delivery circuit completes a predetermined number of shock sets. The AED then remains in the scheduled mode and provides electrotherapy shocks solely between intervals of CPR. In one preferred embodiment, the AED may be programmable to discontinue further reversions after from one to seven shock sets have been completed. The AED may also be programmable to set the number shock sets to infinity, whereupon the cycle will continue until the device is turned off.

An optional embodiment of the AED processor operation is that the processor automatically shifts from continuous to scheduled CPR rescue protocol if an "undecided" determination persists for a predetermined time. This operation would generally occur near the beginning of the AED operation such as at steps 1104, 1106 as shown in FIG. 11. If no such determination persists, the processor will shift from continuous to scheduled mode according to the methods described above.

Another embodiment of the AED uses a sensed number of CPR compressions parameter instead of elapsed time. The sensed number of CPR compressions may be obtained from one or more sources. Electrode noise artifact signals or common mode current (CMC) may be used, external CPR sensing devices such as the Q-CPR device manufactured by Philips Electronics North America, Andover Mass., may be used, or other similar sensors.

The AED and its operation as described above may be embodied in either a semi-automatic device or a fully automatic device. The semi-automatic AED of course includes a user-operated shock button 92 and therefore should include corresponding instructions and indications to press the shock button as appropriate. The fully automatic AED will embody a slightly different set of instructions that include nothing about the shock button but which clearly notify the user of a pending shock and that instructs the user to remain clear of the patient if necessary.

Methods Using Two ECG analysis algorithms, such as ART and PAS

The inventors have recognized that most patients never have a shockable rhythm during a cardiac arrest emergency, so any ECG analysis algorithm could operate for long periods of time without providing a "shock-advised" determination. But the inventors also recognize that the afore described ART algorithm is not as sensitive to detecting a shockable cardiac rhythm as PAS. ART thus has a higher likelihood of missing "true positive" shockable rhythms during CPR. Also, the ART "undecided" determination does not distinguish between "no shock advised" (NSA) and "indeterminate" ECG. For these reasons, it many become important during periods of CPR compressions to periodically confirm the ECG analysis with a different ECG algorithm.

One solution to this problem would simply to use a PAS confirming analysis periodically during the rescue. But this solution is suboptimal because it may unnecessarily increase the overall hands-off time. The inventors have thus recognized that PAS can be used to confirm, but should be used as infrequently as possible and only in those situations where hands-off time has minimal detriment to the patient. Such situations may be at the end of an otherwise scheduled period for CPR compressions, for example.

Figure 14:
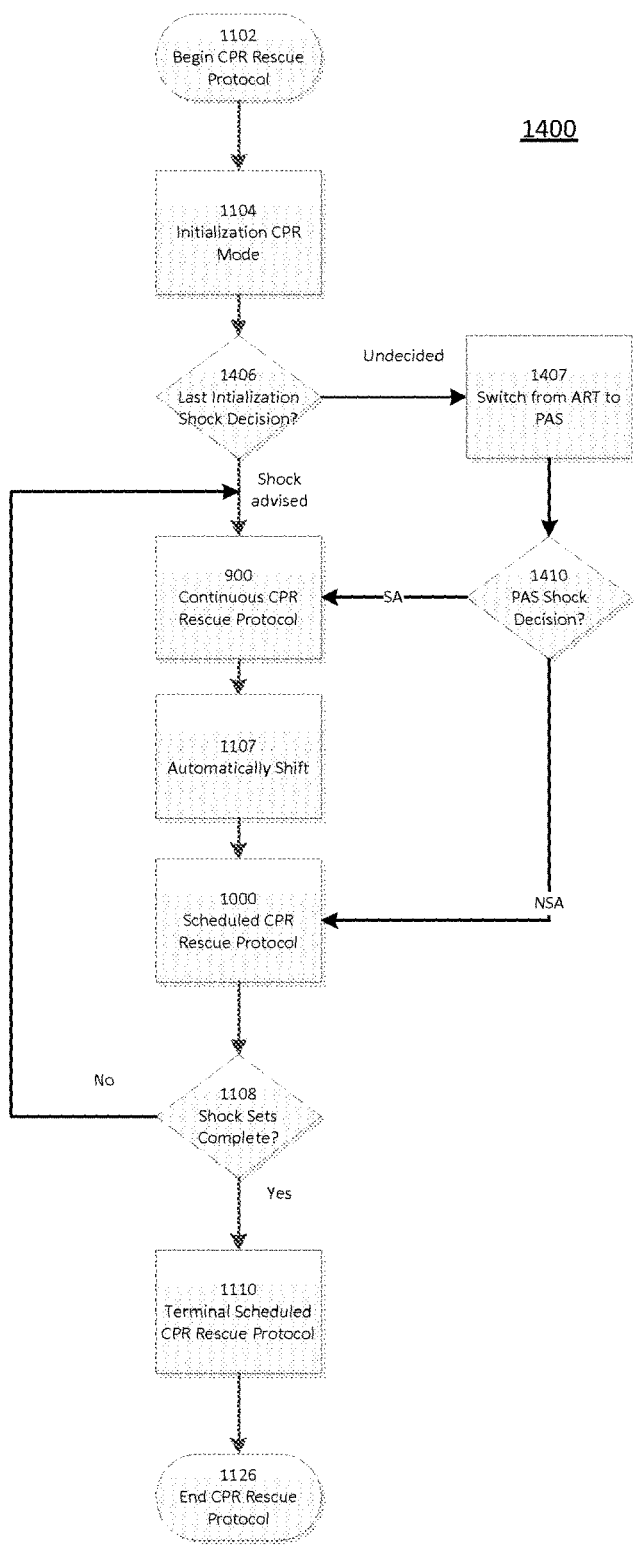
FIG. 14 illustrates a process flow embodiment for a cardiac rescue protocol which automatically shifts between two ECG analysis algorithms based on the progress of the rescue.

FIG. 14 illustrates such a method solution that reduces the problems presented by needlessly interrupting CPR compressions for a confirming analysis. FIG. 14 is similar to FIG. 11. But FIG. 14 illustrates a method that is modified to use both of a first ECG analysis algorithm and a second ECG analysis algorithm. The first ECG analysis algorithm is exemplified by the previously described ART algorithm 200, which is particularly suitable for use in the presence of CPR-related signal noise artifact. The second ECG analysis algorithm is exemplified by the existing PAS algorithm, which is particularly suitable for use in the absence of CPR-related signal noise artifact.

Like the FIG. 11 method, the illustration of FIG. 14 comprises a method 1400 for providing electrotherapy during the application of CPR. The method is enabled at step 1102 in a defibrillator 1 having an ECG signal input 12, a shock delivery circuit 80 and a user interface 18. The device and method also utilize two different ECG analysis algorithms. The first, like ART, is operable to determine one of a "shock advised" (SA) and an "undecided" from the ECG signal while in the presence of a CPR-related signal noise artifact. The second, like PAS, can more specifically determine one of a SA and a "No Shock Advised" (NSA) determination from the ECG signal in the absence of the CPR-related signal noise artifact. The defibrillator in step 1102 senses that the ECG signal input 12, such as electrodes, are attached and thus ready to begin ECG analysis.

The FIG. 14 method proceeds at step 1104 by analyzing the ECG signal with the first ECG analysis algorithm during a first period to determine whether a shockable cardiac rhythm exists. It is preferable that the defibrillator is providing CPR guidance instructions during this period in a scheduled CPR rescue mode of operation. In the event of a SA determination, the defibrillator will prepare to deliver a shock at the end of the step 1104. In addition, the method proceeds at decision step 1406 based on whether the ECG signal indicates a SA or an "undecided" determination. A preferred point for determination is at the end of the first period, although the determination could also be based on an average or count of SA's or the like over the period. Other aspects of steps 1102 and 1104 are previously described relative to FIG. 11 above.

If a SA is determined during the first period of decision step 1406, then the remaining steps of the CPR rescue procedure also correspond to those described in the method of FIG. 11. In particular, following a SA determination, the cardiac rhythm is determined using the first ART ECG analysis algorithm during second and successive periods of continuous CPR 900 and scheduled CPR 1000. Subsequent SA determinations cause the defibrillator to arm for shock and issue CPR/shock delivery instructions according to the type of CPR period. Shock sets may also be employed to shift from continuous to scheduled CPR modes of operation as previously described. Thus an optimized and customized rescue protocol is output from the defibrillator.

Only if step 1406 determines any other than a SA determination is the second ECG analysis algorithm employed. If an "undecided" determination occurs at step 1406, the method automatically switches from the first to the second algorithm at step 1407.

After switching step 1407, the method employs the second ECG analysis algorithm (PAS) to analyze the ECG signal at PAS decision step 1410. Preferably, the defibrillator issues user prompt to "stop CPR" and/or "do not touch the patient" at this step so that the PAS algorithm can effectively analyze in a low-noise environment. Two possible outcomes of PAS decision step 1410 are SA or "No Shock Advised" (NSA). PAS may also issue an "artifact" decision, which is not a topic for this invention, and will not be further discussed.

A determination of SA in PAS decision step 1410 indicates that the ECG may have presented as a shockable rhythm at or near the beginning of the event, i.e. at step 1102, but that the first algorithm failed to sense it. A SA determination at this step is preferably followed by immediate arming and delivery of electrotherapy.

Evidence suggests that a patient with a SA presenting ECG rhythm may benefit from more electrotherapy earlier in the rescue. Thus a SA determination by PAS in step 1410 also causes an automatic switch back to the first ECG analysis algorithm in a continuous CPR rescue protocol 900 that delivers electrotherapy promptly after detection of a shockable rhythm. The continuous CPR rescue protocol 900 then functions as previously described.

But a determination of NSA at step 1410 indicates that the presenting ECG is not shockable. Such patients may benefit from more CPR compressions early in the rescue. Thus, an NSA determination by PAS at step 1410 causes an automatic switch back to the first ECG analysis algorithm in a scheduled CPR rescue protocol 1000 that delivers a greater relative amount of CPR time. The scheduled CPR rescue protocol 1000 and the remainder of the cardiac rescue method then functions as previously described.

It is preferred that the duration of each period in which the PAS second ECG analysis algorithm operates is as short as possible because of the sub-optimal requirement that the rescuer is "hands-off" during the analysis. A typical PAS analysis period is less than about ten seconds, although it may be as short as four seconds. This duration is in most cases shorter than the duration of either a continuous or scheduled mode of CPR using the first ART algorithm. The frequency of the PAS periods is also preferred to be as low as possible for the same reasons. Thus, the method steps require a switch to the "hands-off" PAS analysis only when necessary to do so.

Figure 15:
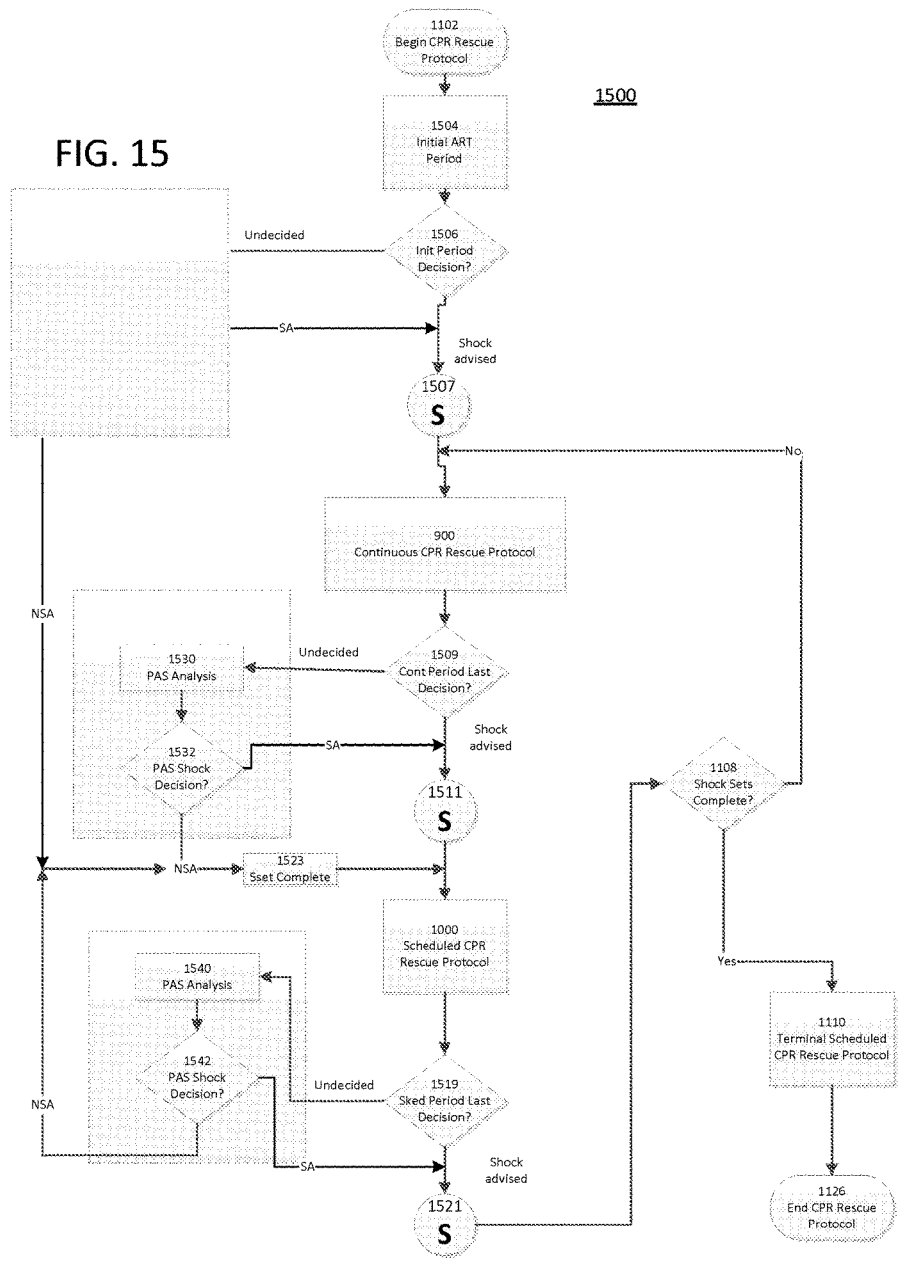
FIG. 15 illustrates a detailed process flow method for shifting between two ECG analysis algorithms based on the progress of a cardiac rescue.

An alternative and more detailed view of the inventive method is illustrated in FIG. 15. The FIG. 15 method more clearly illustrates how electrotherapy is provided with a minimum of interruptions to CPR, even after an initial ART algorithm period of CPR 1504. After activating the defibrillator and applying electrodes at step 1102, an initialization period at step 1504 immediately begins, comprising the issuing of prompts for applying CPR compressions and using the first ECG analysis algorithm is. Step 1504 is preferably a scheduled CPR rescue mode of operation having uninterruptible CPR regardless of the ART rhythm determination. Step 1504 is even more preferably of a relatively short duration of about 20-30 seconds, or enough time to apply a minimum number of about 30 CPR chest compressions. The method may sense the number of chest compressions or the amount of time, after which the ART rhythm determination is finalized at decision step 1506. Step 1504 thus provides all patients the benefit of some period of uninterrupted chest compressions at the start of the rescue.

If SA is indicated at decision step 1506, then the method immediately enters an arming for electrotherapy step 1507, allowing for the delivery of a therapeutic shock. Following step 1507, the method enters a second period, continuous CPR mode of rescue protocol 900, which proceeds as described previously. The duration of the second period 900 may be about two minutes, but may also be configurable prior to device activation. Then the method proceeds to continuous mode terminal decision step 1509.

If a SA determination is present at step 1509, the method proceeds as previously described for the FIG. 11 method. The method enters an arming for electrotherapy step 1511, allowing for the delivery of a therapeutic shock. Then the mode of operation with the first ART algorithm automatically switches to a scheduled CPR rescue mode of operation at step 1000. Step 1000 proceeds as previously described by prompting the user with CPR instructions while analyzing the ECG rhythm in the background and by deferring any action from an SA determination to the end of the period. The scheduled period 1000 may be of about two minutes duration.

If a SA determination is present at the end of step 1000, i.e. at decision step 1519, the method enters an arming for electrotherapy step 1521, allowing for the delivery of a therapeutic shock. After the shock is delivered, the method may loop back to the continuous mode step 900 if the shock sets are not yet completed at checking step 1108. If shock sets are complete, the method switches to the terminal scheduled CPR rescue protocol at step 1110, where it remains until the end of the rescue at step 1126.

It can be seen by FIGS. 14 and 15 that as long as a SA state can be determined by the first ART algorithm, the method proceeds without the need for the second PAS analysis. Thus, the method minimizes the "hands-off" time that is required for PAS.

If however the first ART algorithm instead determines an "undecided" state at any of the decision steps 1506, 1509, and 1519, the method automatically switches at respective steps 1520, 1530, and 1540 to the second PAS algorithm for a further determination. Steps 1520, 1530, and 1540 issue "hands-off" instructions and then analyze the ECG. These PAS periods may be of short duration of ten seconds or less in order to minimize "hands-off" time.

As can be seen in FIG. 15, if any of the PAS analysis determinations are SA, decision steps 1522, 1532, and 1542 immediately return the method to the first ART algorithm sequence at the respective point of departure, i.e. after step 1506, step 1509, or step 1519. The reasoning for this path is that ART analyses are generally preferable to PAS analyses because of the overall reduced hands-off time. Thus the method should switch back to ART whenever possible.

Also seen in FIG. 15 is if any of the PAS analysis determinations are NSA, then the method automatically shifts back to the first ART algorithm operating in a scheduled CPR mode of operation at step 1000. The reasoning for this path is that PAS has confirmed that the ECG is presenting a non-shockable rhythm, and so for such patients a period of uninterrupted CPR is more beneficial.

An optional step 1523 after any PAS determination of NSA sets the current shock set as completed. This optional step thus moves the method 1500 closer to a shift at step 1108 to a terminal and permanent scheduled CPR rescue mode of operation at step 1110. The reason for this is the inventor discovery that an eventual shift to a higher proportion of CPR-to-shock in the scheduled mode may be more beneficial to a patient that indicates an NSA ECG rhythm somewhere earlier in the rescue.

Apparatus Interleaving PAS and ART Algorithms in the Continuous and Scheduled Modes of Operation A device, such as the AED shown in FIGS. 6 and 8 above, may operate according to any of the afore described methods for interleaving CPR with electrotherapy while incorporating two different ECG analysis algorithms. The AED is preferably controlled by controller 30 which includes a processor 34 and an ECG analyzer 32. Controller 30 is in communication with the ECG signal input 12, user interface 18, and memory 40 to provide instructional guidance to the user in the conduct of a cardiac rescue. Controller 309 also is in controlling communication with a shock delivery circuit 80 that delivers an electrotherapy output.

Memory 40 stores instructions related to both of a first ECG analysis algorithm that is operable to determine one of a "shock advised" (SA) and "undecided" determination from the ECG signal in the presence of a CPR-related signal noise artifact from the input, and a second ECG analysis algorithm that is operable to determine one of a SA and a "No Shock Advised" (NSA) determination from the ECG signal in the absence of CPR-related signal noise artifact from the input. Memory 40 also stores instructions related to a CPR rescue protocol that includes at least two periods for providing CPR compressions.

Controller 30 in particular operates the AED in the sequence of continuous CPR rescue mode of operation and the scheduled CPR rescue mode of operation as previously described. In addition, controller 30 issues guidance via the user interface 18 and automatically prepares the shock delivery circuit 80 for delivering electrotherapy responsive to a SA determination from either of the first and second ECG analysis algorithms. Finally, and because the first ECG analysis algorithm may have a lower sensitivity to shockable ECG rhythms during periods with CPR-related noise, the controller 30 is further operable to always automatically switch from the first to the second ECG analysis algorithm at an end of one of the periods during which the first ECG analysis algorithm determines any other than a SA determination. Thus, the use of the second ECG analysis algorithm, which requires "hands-off" time that is sub-optimal for a cardiac arrest patient, is placed into use only when necessary.

Other device behavioral aspects of the AED reflect the previously described methods. For example, if a SA is determined after automatically switching from the first to the second ECG analysis algorithm, the AED controller may automatically switch back to the first algorithm and to a continuous CPR rescue mode of operation. On the other hand, if a NSA is determined after automatically switching from the first to the second ECG analysis algorithm, the AED controller may automatically switch back to the first algorithm and to a scheduled CPR rescue mode of operation.

The second ECG analysis algorithm may be the PAS algorithm which can characterize an ECG rhythm in less than 10 seconds. The duration of each period in which PAS operates should thus be no be longer than that.

The AED may functionally include the initialization period that occurs just after activating the AED and ECG signals are being received. The initialization period comprises a scheduled CPR rescue mode of operation using the first ECG analysis algorithm, wherein the scheduled CPR rescue mode of operation provides a predetermined period of uninterruptible CPR regardless of the determination. The length of the initialization period may be relatively short as compared to subsequent rescue protocol periods. For example, the initialization period may end at a sensed number of CPR compressions, wherein the sensed number is about 30 and where in existing CPR protocols would be completed in less than 30 seconds. Alternatively, the initialization period may be pre-determined at a duration of between about 20 and 30 seconds.

The AED and its operation as described above may be embodied in either a semi-automatic device or a fully automatic device. The semi-automatic AED of course includes a user-operated shock button 92 and therefore should include corresponding instructions and indications to press the shock button as appropriate. The fully automatic AED will embody a slightly different set of instructions that include nothing about the shock button but which clearly notify the user of a pending shock and that instructs the user to remain clear of the patient if necessary.

Analyze Button for Truncating CPR

There may be situations in which an experienced user may desire to truncate the ongoing AED protocol in order to quickly enter another mode of operation, and in particular to more quickly deliver a defibrillating shock. The invention simplifies the truncating action by offering just a single button to do so. The AED automatically selects the response to the button press that is most beneficial to the patient, based on the underlying ECG analysis.

A defibrillator (AED) and method for using a defibrillator incorporates a user activated button which truncates an ongoing and otherwise uninterruptible CPR compressions period to immediately perform a different defibrillator-related function. The truncation button is particularly useful in the scheduled CPR rescue mode of operation 1000, previously described. Thus the operation is simpler for the user, reduces the potential for protocol-following errors, and minimizes delay caused by confusion during the event.

One exemplary AED having a truncation feature may use two different ECG analysis algorithms which have different sensitivities to a shockable cardiac rhythm. A press of the truncation button may automatically shift from a first ECG analysis algorithm to a second ECG analysis algorithm having a higher sensitivity. The button may also allow truncation of ongoing analysis and CPR for immediate preparation for electrotherapy if an underlying shockable cardiac rhythm has already been detected.

The AED and method reduce the hands-off time between CPR compression periods and electrotherapy, even when the truncation button is activated. By way of example, if the underlying ECG analysis indicates a shockable rhythm, the AED may be charging for therapy in the background, while indicating "Charge" or "Analyze" on the truncation button. Thus if the user presses the truncation button, the AED may be ready to deliver electrotherapy immediately.

The AED with the controlling features as previously described changes its response to a sensed press of the truncation button based on the current state of the patient ECG. If the AED determines the underlying ECG to be shockable, it may change a contextual label for its button to "Charge". When the AED senses that the truncation button has been pressed, the AED immediately charges for a defibrillating shock. If the ECG is non-shockable, the button label may instead appear as "Analyze". Pressing the same button would cause the AED to immediately switch from a first ART algorithm to a second PAS algorithm to confirm the existing state. Alternatively, a sensed truncation button press may immediately cause the AED to issue a prompt to "stay clear of the patient" in order to increase the sensitivity of the current ART algorithm analysis.

Figure 16:
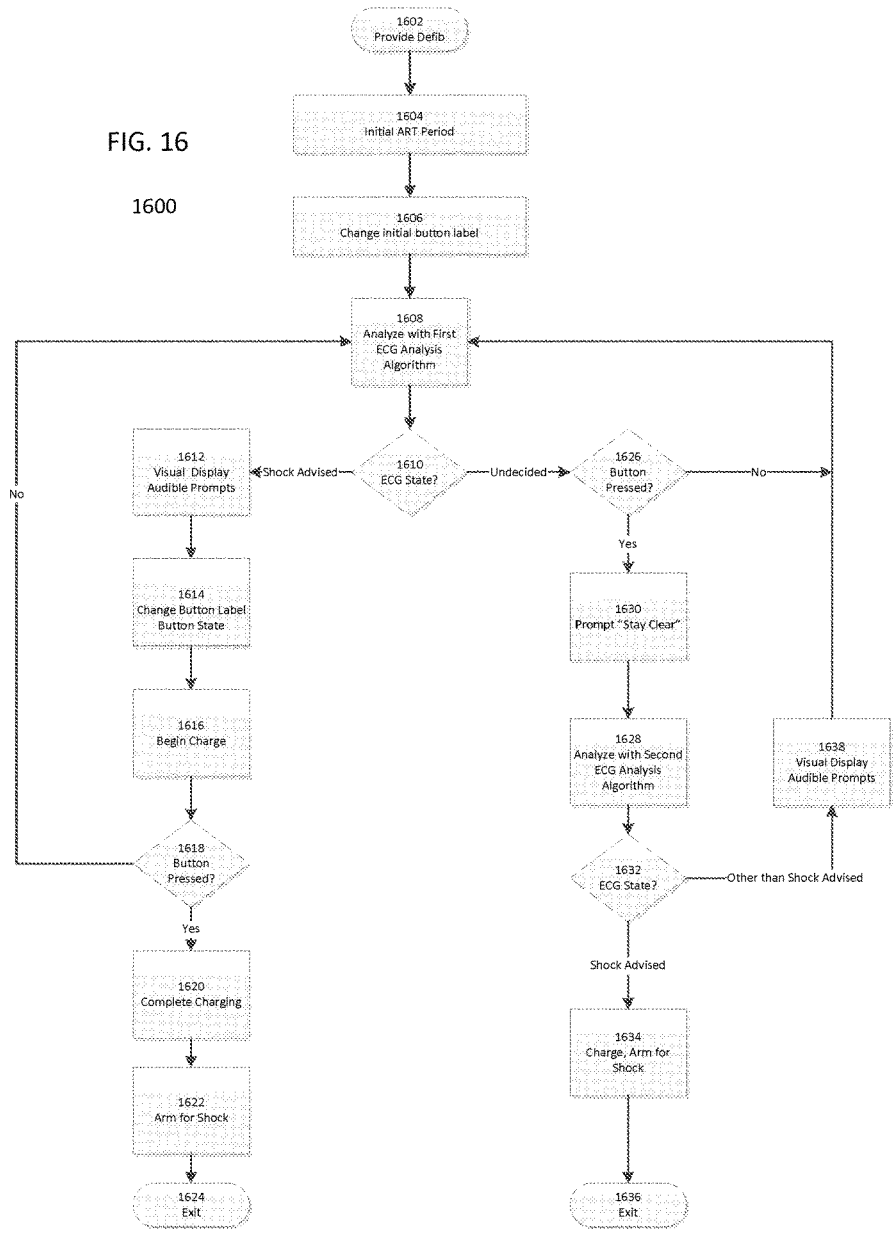
FIG. 16 is a flow chart that illustrates a method for truncating CPR in favor of providing electrotherapy during a cardiac rescue.

The method steps shown in FIG. 16 may be better understood by also referring periodically to the particular visual displays and truncation buttons shown in FIGS. 17a through 17d. FIGS. 17a, 17b, 17c, and 17d show various graphic displays 1706, 1714, 1718, and 1728 corresponding to an AED visual display such as visual display 802. Each of the FIGS. 17a-d shares a common general arrangement. One or more guidance and information messages are displayed on an upper banner area. A progress bar such as a CPR progress bar may be placed adjacent the upper banner area. In the center of the display is an area for showing an ongoing ECG trace or guidance graphics for placing electrodes, hands on chest for CPR, and the like. The bottom portion of the display preferably includes contextual labels, exemplified by contextual labels 804, 806, that may change based on the particular operating state of the defibrillator and the underlying ECG analysis.

In a preferred embodiment, input buttons 854, 856 are disposed immediately adjacent to displays 1706, 1714, 1718, and 1728, and next to contextual labels 804, 806 respectively. In an alternate embodiment, visual display 802 may be a touch sensitive display such that the input button 854,856 effectively underlies its respective contextual label 804,806.

Now turning to the FIG. 16 flow chart, an exemplary method 1600 for truncating CPR for the purpose of providing immediate electrotherapy is shown. The method begins at providing step 1602 of a defibrillator having features which work in concert to perform the method. Namely, the defibrillator includes an ECG signal input 12, a user interface 818 including an input button 854 and a visual display 802, a shock delivery circuit 80, and a first ECG analysis algorithm that is operable to determine a shockable cardiac rhythm from the ECG signal in the presence of a CPR-related signal noise artifact from the input. A defibrillator such as AED 800 is but one example of the provided apparatus.

AED 800 may include several different operating mode configurations which are preconfigured prior to use. Any or all of these modes may be maintained in the AED memory 40. Exemplary operating modes are Advanced Mode, CPR First Mode, and Semi-Automatic mode. Each operating mode may differ slightly as to the circumstances in which a truncation button may appear.

Advanced Mode is a protocol that permits a responder more control over when the AED begins ECG rhythm analysis and arming for shock delivery. The Advanced Mode, for example, may be configured to provide an "ANALYZE" and/or a "CHARGE" option button at particular periods during the protocol. Pressing the "ANALYZE" option button may initiate an immediate Hands-Off Analysis with PAS. Pressing the "CHARGE" button may permit one or more of a Hands-Off Analysis, charging of the high voltage energy storage source 70, and shock delivery.

After the AED 800 activates and begins receiving an ECG signal input 12, it begins to analyze the ECG signal with the first ECG analysis algorithm (ART) during an optional initial period 1604. Initial period 1604 is preferably similar to step 1104 operating in an uninterruptible CPR compressions mode of operation as described previously. During this short initial period 1604, however, the truncation button may be active to immediately exit from CPR compressions to an ECG analysis or for arming for electrotherapy. The reason for enabling the truncation button at period 1604 is to allow for situations where the operator recognizes that adequate CPR has been provided prior to the arrival and activation of the AED.

Figure 17A:
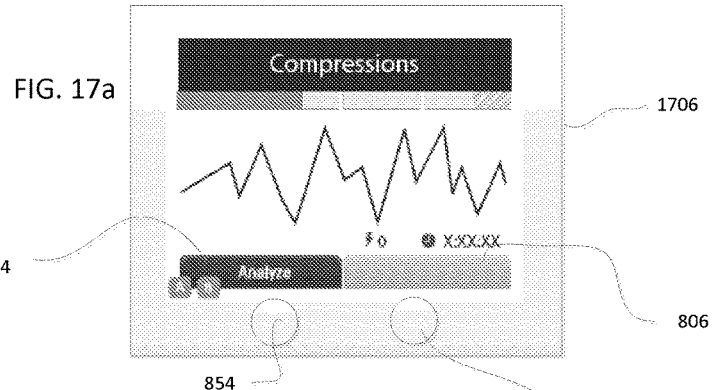

The visual display during initial period 1604 preferably corresponds to an "analyze-undecided" screen 1706 as shown in FIG. 17a. The AED displays a contextual label of "Analyze" adjacent to truncation button 854. If the operator wishes to truncate the initial compressions period for analysis, she presses the truncation button 854. When the AED senses the button press, it immediately issues user prompts to "stay clear of the patient" and begins an ECG analysis using the $2^{nd}$ PAS ECG analysis algorithm. During this time, the AED may display an "analyze-stay clear" screen 1728 from FIG. 17c.

Label step 1606 follows optional step 1604. Label step 1606 sets the initial contextual label that corresponds to a previously analyzed ECG at the initiation of the ART analysis period 1608. Preferably, the AED display the "analyze-undecided" screen 1706 in order to establish the next steps in the protocol.

First analyzing period step 1608 follows label step 1606. Step 1608 includes the device analyzing the ECG signal with the first (ART) ECG analysis algorithm and preferably in the uninterruptible scheduled mode of CPR. Step 1608 thus includes the defibrillator issuing audible and/or visual prompts to continue CPR compressions. The analyzed ECG signal during this period will be either "undecided" or "shock advised" as shown at decision step 1610. Also during this first analyzing period, the defibrillator controller 30 begins to monitor for an activation of input button 854.

As can be seen in FIG. 16, the next steps in the method 1600 depend on the underlying analyzed ECG signal. If the decision at steps 1608, 1610 are "shock advised", the left branch of the method proceeds. The AED may change the upper portions of display 1706 to indicate the directive text at display step 1612. An information message such as "shock advised" and/or a guidance message of "Press Analyze Button" as shown on "truncation available—shockable rhythm" screen 1714 of FIG. 17b may appear. Alternatively, a guidance message of "Press Charge Button" as shown on "truncation available—charge" screen 1718 of FIG. 17d may appear. Audible guidance at this step 1612 is also possible but is less preferable than solely visual guidance in order to prevent undue distraction from the task of providing CPR compressions. Alternatively, step 1612 may include issuing an audible instruction that the truncation button is active.

Figure 17B:
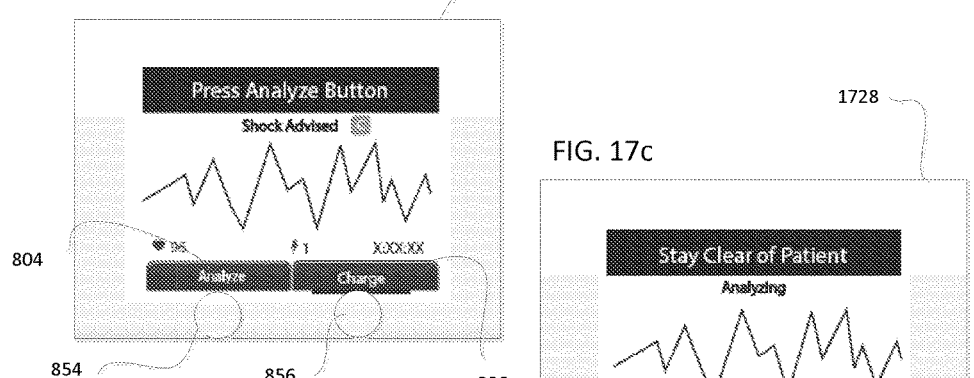
Figure 17C:
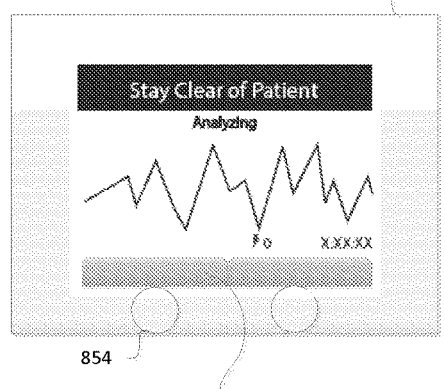
Figure 17D:
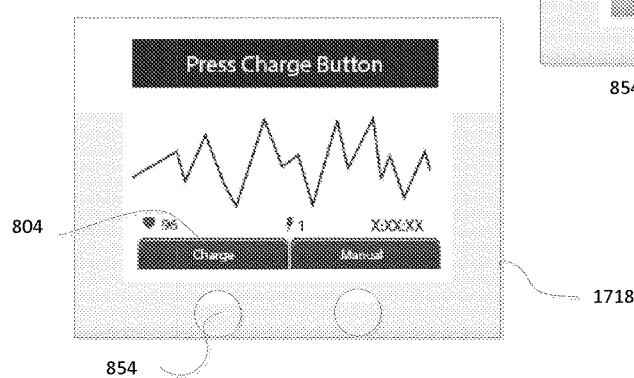

A "shock advised" decision at step 1610 may also initiate a change in contextual label 804 at contextual label change step 1614. The contextual label 804 may be changed from the "Analyze" indication to a "Charge" indication. Alternatively, the "Charge" contextual label/button combination could be displayed with the "Analyze" indication at the $2^{nd}$ contextual label 806 adjacent the second configurable button 856 as seen in FIG. 17b. Then the AED may initiate a background charging of the HV energy storage source 70 at background charging step 1616.

With the analyzed ECG signal indicating a shockable rhythm, the AED monitors for a truncation button activation at sensing step 1618. If no activation occurs, the method 1600 merely loops back to analyze step 1608 for continued monitoring during the period.

If the AED senses the truncation button activation at sensing step 1618, the AED immediately proceeds to an armed shock delivery state. Charging of the HV energy storage source 70 is completed if necessary at charging step 1620 and the shock button is armed at arming step 1622. Appropriate visual and audible prompts are provided along the way to guide and inform the user.

Some users prefer to omit background charging of the HV circuitry whenever CPR compressions are being provided. The AED thus can be pre-configured to omit background charging step 1616. In this configuration, when the AED senses button activation at sensing step 1618, it immediately proceeds to an operating state of charging the shock delivery circuit at charging step 1620. The AED then arms itself for shock at arming step 1622.

Exit step 1624 exits the method after the AED is armed. Following exit step 1624, other methods may proceed such as looping back to step 1608, entering different protocols, or the like.

The right branch of the method proceeds if the decision at steps 1608, 1610 is "undecided." "Undecided" is a determination of an other-than-shockable rhythm, which includes non-shockable rhythms as well as indeterminate rhythms. The first ECG analysis algorithm may also be unable to distinguish between a shockable and non-shockable cardiac rhythm, especially in the presence of CPR-related signal noise, and thus would return an indeterminate "undecided" decision. The AED preferably displays the "Analyzing-undecided" visual display 1706, the "Analyze" contextual label 804, and active monitoring for a sensed press of truncation button 854 at this state. Truncation button sensing step 1626 actively monitors for the sensed press of the truncation button without any further prompting of the operator. It can be seen at sensing step 1626 that the absence of a sensed press merely loops the process back to the analyzing step 1608 for continued monitoring.

When the AED senses the truncation button press at sensing step 1626, the method immediately interrupts the ongoing CPR compressions protocol with visual and audible prompts to stay clear of the patient. The "analyzing-stay clear" screen 1728 of FIG. 17c may be displayed at prompting step 1630 with the corresponding guidance to "stay clear of the patient" for further ECG analysis. Audible prompts are also preferably issued at prompting step 1630.

In a preferred embodiment, the AED is provided with the second ECG analysis algorithm (PAS). At analyzing step 1628 and after "stay clear" prompts from step 1630 have issued, the second ECG analysis algorithm analyzes the ECG to determine if the cardiac rhythm is shockable or non-shockable. If PAS determines a "shock advised", i.e. a shockable cardiac rhythm, then the method at charging/arming step 1634 automatically begins charging and arming the shock delivery circuit for the immediate delivery of electrotherapy. Exit step 1636 exits the method after the AED is armed. Following exit step 1636, other methods may proceed such as looping back to analyzing step 1608, arming for additional shocks, entering different protocols, or the like.

If PAS determines a "no-shock advised" at analyzing step 1628, 1632, the AED conveys the result and corresponding guidance to the user at prompting step 1638. Preferably, audible and visual instructions are provided to resume CPR. ECG analysis also resumes at analyzing step 1608 using the first ECG analysis algorithm.

An alternative embodiment for the right branch of method 1600 is to continue the use of the first ECG analysis algorithm after the "stay clear" prompts at prompting step 1630. The increased sensitivity of the first algorithm during quiet periods may allow detection of a shockable rhythm after the CPR noise signal component is eliminated. Analyzing step 1628 thus may be used with the first ECG analysis algorithm instead of the second ECG algorithm. Subsequent steps 1632, 1634, 1636, 1638 may be similar to those previously described under this embodiment.

An AED with the elements as previously described may adopt the above method having a truncation button. Accordingly, the AED necessarily includes a controller 30 which is operable to set the operating state of the defibrillator responsive to both of a sensed actuation of the input truncation button 854 and the underlying analyzed ECG signal.

The AED response to a sensed press of the Analyze option button may also vary somewhat depending on the configuration of the device. For example, the Table 1 chart illustrates the functionality of the button during various types of configurations and underlying ECG states:

TABLE 1

| AED configuration | Patient ECG state | Press analyze button function (contextual label and function) |
| --- | --- | --- |
| CPR first | shockable | Label: Charge Fn: charge for shock. |
| CPR first | Non-shockable | Label: Analyze Fn: conduct PAS analysis |
| Analysis through CPR (continuous) | shockable | Button not available or PAS analysis |
| Analysis through CPR | Non-shockable | Label: Analyze Fn: conduct PAS analysis |
| Scheduled (uninterruptible CPR) | shockable | Label: Charge Fn: charge for shock. |
| Scheduled (uninterruptible CPR) | Non-shockable | Label: Analyze Fn: conduct PAS analysis |
| Off | Non-shockable | Analyze button as exists under PAS. |
| Off | shockable | Analyze button as exists under PAS. |

Additional Embodiment of the Invention—Confidence Analyzer

FIG. 18 illustrates a conceptual embodiment of a confidence indicator for the ART algorithm as previously described in FIG. 5. Decision surface 510 delineates a VF or "shock advised" zone within the boundary from an "undetermined" zone outside of the boundary. A region of low confidence shockable rhythms 512 is shown as defined by decision surface 510 and a boundary of a predetermined confidence threshold 511. A shockable value pair 521 within the region exemplifies an ART decision of VF but of low confidence. The value pair indicating VF 520 in contrast exemplifies an ART decision of VF with high confidence. As will be seen, these conditions of shockable VF will be treated differently in the method and apparatus behavior.

Also shown in FIG. 18 are CLAS/FLATS value pairs indicating "undecided" decisions. Value pair 530 is distal from decision surface 510 and thus is likely to be of high confidence. Value pair 531 is proximate decision surface 510 and thus is likely to be of low confidence. In a preferred embodiment of the invention, however, no difference in device behavior or method results between these pairs because the additional risk to the patient from a "false negative" ART decision is very low. Although just two dimensions are shown in FIG. 18, it is understood that additional dimensions may define the decision surface 510.

FIG. 19 illustrates a method 1900 for ECG analyzing using ART and a confidence analysis during CPR. ART analyzing during CPR step 1902 generally encompasses the FIG. 2a steps of receiving ECG signal 202 through the analyzing step 210, including the step of obtaining an ECG signal data stream buffer 204. Analyzing step 210 divides each ECG data stream buffer from step 204 into an undecided "non-shockable" rhythm 1905 or into a VF "shockable" cardiac rhythm 1903, 1904.

Concurrent with the analyzing step 210 is a confidence level calculating step 210'. Confidence level step 210' further identifies each data pair as either a low shockable cardiac rhythm 1904, e.g. of CLAS/FLATS pair 521, or a high confidence cardiac rhythm 1903, e.g. of CLAS/FLATS pair 520. Many methods for estimating confidence are known in the art, and the shown method of FIG. 18 is but one example.

Only if the confidence level of the shock decision is less than a predetermined threshold, e.g. within low confidence region 512, are the shock decision criteria adjusted at criteria adjusting step 214'. The adjusting is also shown at adjusting step 1907. One embodiment of a criteria adjusting is to increase the threshold number of sequential ECG data stream buffers analyzed to be shockable before a shock decision can be made. For example, the threshold number may be increased from the previously described three shock-determined buffers to four. Another embodiment of a criteria adjusting may be to analyze in a noise free environment. Thus, this embodiment may additionally entail a step of issuing a user prompt via the user interface to stop CPR prior to the second analysis. The prompt could occur immediately upon the determination of a low confidence shockable rhythm or at the end of the CPR period. A third embodiment of a criteria adjusting step may also be to switch from analyzing with the ART algorithm to a second algorithm, e.g. PAS, for confirming analysis of the ECG buffer and subsequent buffers. The confirming action using the modified criteria at step 1907 provides a higher confidence shock decision or a confirming shock decision back to shockable rhythm state/step 1903.

The method for processing shockable decisions then proceeds as previously described. Shock deciding step 214 activates the electrotherapy delivery circuit, wherein the electrotherapy circuit is automatically armed and appropriate user prompts are issued to guide the shock delivery. This step is summarized by the arming and delivery step 1916.

FIG. 19 also illustrates the process and device behavior for ART non-shockable rhythm determinations. In a preferred embodiment, both low and high confidence decisions are treated equally. CPR is continued without pausing for further analysis and without modifying the shock criteria at step 1906. But an optional embodiment treats low confidence indeterminate decisions, e.g. indeterminate CLAS/FLATS pair 531, similar to low confidence shock decisions. Step 1907 would adjust criteria for improving these low confidence decisions as well.

Now with reference to FIG. 2, FIG. 18, and FIG. 19, the previously described AED 10 that uses the first algorithm (ART) is modified to include a confidence analyzer circuit 32'. The AED input 12, user interface 18 and ECG analyzer 32 is as previously described. The confidence analyzer circuit 32' determines a confidence of the shock/no-shock decision when using the ART algorithm. Although shown as part of ECG analyzer 32, confidence analyzer circuit 32' could be arranged as part of processor 34, or as a stand-alone circuit.

AED 10 with confidence analyzer 32' functions according to the previously described method of FIG. 19. If the confidence analyzer 32' determines that the confidence level of a shockable cardiac rhythm is low, i.e. less than a predetermined confidence threshold, then AED processor 34 executes software instructions to adjust the shock decision criteria according to the embodiments described for step 1907. Processor 34 then decides that a shock is to be delivered based upon the adjusted shock decision criteria and responsively proceeds to arm the AED electrotherapy delivery circuit.

Processor 34 additionally and optionally controls the user interface to issue user prompts to "stop CPR" as previously described, and also may control the user interface to display or prompt an indication of the confidence level in the then-current ECG analysis determination. This provides the user with additional assurance that the analysis circuit output is accurate and useful.

Additional Embodiments of the Invention

Another embodiment is an AED which tracks the progress of a sensed ECG, and alters its subsequent protocol based upon changes in the sensed ECG. The AED distinguishes between secondary VF, refractory VF, and refibrillation, and provides a different therapeutic guidance/response for each case. In the example of secondary VF, the AED delays arming for a defibrillating shock in order to allow additional CPR, or until a Vrhythm score indicates a higher probability of shock success. In the example of refractory VF, the AED may advise to transport the patient to advanced cardiac care centers instead of continuing an unsuccessful regimen of CPR and shocks at the scene. In the example of refibrillation, the AED may advise to interrupt CPR and shock as soon as possible.

Another embodiment is an AED having an analysis option that uses a trans-thoracic impedance channel to indicate if CPR is actually on-going (or not) and then determines which of two algorithms should run depending on that state. If the AED detects CPR, then it uses an ART analysis. If the AED detects no ongoing CPR, then it switches to a PAS analysis. The functionality depends on the presence or absence of compressions and ensures the algorithm with the best sensitivity and specificity for the conditions is used. This automated switching between algorithms may be particularly beneficial to lay responders who may not follow standard CPR protocols as well as professional responders.

Additional modifications to the device, method, and displays as described above are encompassed within the scope of the invention. For example, various configurations of the user interface displays and aural indicators which fulfill the objectives of the described invention fall within the scope of the claims.

What is claimed is:

1. An automated external defibrillator (AED) for use during cardiopulmonary resuscitation (CPR) comprising:
   an input of an ECG signal;
   a user interface having at least one of an aural instruction output and a visual display;
   an ECG analyzer in communication with the input and operable to determine a shockable cardiac rhythm in the presence of CPR-related signal noise artifact from the input;
   a confidence analyzer operable to determine a confidence level in the determined shockable cardiac rhythm; and
   a processor in communication with the user interface, the ECG analyzer and the confidence analyzer, the processor operable to execute software instructions to adjust a shock decision criteria if the confidence level is less than a predetermined confidence threshold, decide that a shock is to be delivered by an electrotherapy delivery circuit based on the adjusted shock decision criteria, and arm an electrotherapy delivery circuit responsive to a shock delivery decision,
      wherein the predetermined confidence threshold is a distance from a decision surface which is constructed from at least corresponding pairs of one of a CLAS score and a FLATS score, and
   wherein the CLAS score is comprised of a score from an ECG buffer from the ECG signal filtered at a center frequency of about 25 Hertz and the FLATS score is comprised of a second score from the ECG buffer filtered at a center frequency of about 35 Hertz.

2. The AED of claim 1, wherein the software instructions to adjust a shock decision criteria comprise instructions to issue a user prompt to stop CPR via the user interface and to decide that a shock is to be delivered based on a second ECG analyzer output.

3. The AED of claim 2, wherein the software instructions to issue a user prompt to stop CPR via the user interface are executed prior to the end of a predetermined CPR period.

4. The AED of claim 2, wherein the software instructions to issue a user prompt to stop CPR via the user interface are executed after the end of a predetermined CPR period.

5. The AED of claim 1 wherein the software instructions to adjust a shock decision criteria comprise increasing a minimum number of a shockable cardiac rhythm determinations from the ECG analyzer.

6. The AED of claim 5, wherein the minimum number is increased from three to four.

7. The AED of claim 1, wherein the processor controls the user interface to issue an indication of the confidence level in the determined shockable cardiac rhythm.

8. A method for controlling an electrotherapy output from a defibrillator, comprising the steps of:
   receiving an ECG signal data stream from two or more external electrodes in electrical contact with a patient, the ECG signal data comprising a cardiac signal characterized by corruption from a CPR compressions noise artifact;
   obtaining an ECG signal data stream buffer, the buffer corresponding to a predetermined time segment;
   analyzing the ECG signal data stream buffer to determine a shockable cardiac rhythm with a first ECG analysis algorithm;
   calculating a confidence level of the determined shockable cardiac rhythm;
   adjusting a shock decision criteria if the confidence level is less than a predetermined confidence threshold, wherein the predetermined confidence threshold is a distance from a decision surface;
   deciding that a shock is to be delivered by an electrotherapy delivery circuit based on the analyzing step and the adjusting step; and
   arming an electrotherapy delivery circuit responsive to the deciding step.

9. The method of claim 8, wherein the deciding step is further based on a plurality of analyzing steps of different ECG signal data stream buffers, and further wherein the adjusting step comprises increasing a criteria of a minimum number of analyzing steps required for a shock decision.

10. The method of claim 9, wherein the adjusting step increases the minimum number of analyzing steps from three to four.

11. The method of claim 8, wherein the adjusting step further comprises switching from using the first ECG analysis algorithm to using a second ECG analysis algorithm, and following the adjusting step comprising the steps of;
   receiving a second ECG signal data stream comprising a cardiac signal without corruption from a CPR compressions noise artifact;
   obtaining a second ECG signal data stream buffer, the buffer corresponding to a second predetermined time segment; and
   analyzing the second ECG signal data stream buffer to determine a shockable cardiac rhythm with the second ECG analysis algorithm,
   wherein the deciding step that a shock is to be delivered by an electrotherapy delivery circuit is further based on the analyzing the second ECG signal data step.

12. The method of claim 11, further comprising the step of issuing a user prompt 219 to stop CPR just prior to the receiving a second ECG signal data stream step.

13. The method of claim 12, wherein the issuing step occurs prior to the end of a predetermined CPR period.

14. The method of claim 12, wherein the issuing step occurs at the end of a predetermined CPR period.

* * * * *